US009248280B2

(12) United States Patent
Moffitt et al.

(10) Patent No.: US 9,248,280 B2
(45) Date of Patent: Feb. 2, 2016

(54) CLOSED-LOOP FEEDBACK FOR STEERING STIMULATION ENERGY WITHIN TISSUE

(75) Inventors: Michael Adam Moffitt, Valencia, CA (US); David K. L. Peterson, Saugus, CA (US); Paul Milton Meadows, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 2579 days.

(21) Appl. No.: 11/982,704

(22) Filed: Nov. 2, 2007

(65) Prior Publication Data

US 2009/0118787 A1 May 7, 2009

(51) Int. Cl.
*A61N 1/36* (2006.01)
*A61N 1/05* (2006.01)
*A61N 1/372* (2006.01)

(52) U.S. Cl.
CPC .......... *A61N 1/0553* (2013.01); *A61N 1/36082* (2013.01); *A61N 1/36185* (2013.01); *A61N 1/37235* (2013.01); *A61N 1/0531* (2013.01); *A61N 1/0534* (2013.01)

(58) Field of Classification Search
CPC ........................ A61N 1/36082; A61N 1/36185
USPC ....................................... 607/45–47, 117, 118
See application file for complete search history.

(56) References Cited

U.S. PATENT DOCUMENTS

| 4,328,813 A | 5/1982 | Ray |
| 5,358,514 A | 10/1994 | Schulman et al. |
| 5,464,446 A | 11/1995 | Dreessen et al. |
| 5,683,422 A | 11/1997 | Rise |
| 5,807,397 A | 9/1998 | Barreras |
| 5,820,588 A | 10/1998 | Howard, III |
| 5,843,150 A | 12/1998 | Dreessen et al. |
| 5,927,277 A | 7/1999 | Baudino et al. |
| 6,016,449 A | 1/2000 | Fischell et al. |
| 6,128,537 A | 10/2000 | Rise |
| 6,134,477 A | 10/2000 | Knuteson |

(Continued)

FOREIGN PATENT DOCUMENTS

| EP | 0 911 061 A2 | 4/1999 |
| EP | 0 911 061 A3 | 11/1999 |

(Continued)

OTHER PUBLICATIONS

PCT International Search Report for PCT/US2008/081848, Applicant: Boston Scientific Neuromodulation Corporation, Form PCT/ISA/210 and 220, dated Mar. 27, 2009 (8 pages).

(Continued)

*Primary Examiner* — Tammie K Heller
(74) *Attorney, Agent, or Firm* — Faegre Baker Daniels LLP

(57) ABSTRACT

Methods, systems, and external programmers provide therapy to a patient having a dysfunction. In one aspect, electrical energy is conveyed between electrodes to create a stimulation region in tissue adjacent the electrodes. Physiological information from the patient is acquired and analyzed, and a locus of the stimulation region is electronically displaced relative to the tissue based on the analysis of the acquired physiological information. In another aspect, electrical energy is delivered to tissue of the patient in accordance with one or more stimulation parameters. A cognitive brain signals is sensed and analyzed, and the stimulation parameter (s) are modified based on the analysis of the cognitive brain signal.

30 Claims, 13 Drawing Sheets

(56) References Cited

U.S. PATENT DOCUMENTS

| | | |
|---|---|---|
| 6,321,104 B1 | 11/2001 | Gielen et al. |
| 6,484,059 B2 | 11/2002 | Gielen |
| 6,516,227 B1 | 2/2003 | Meadows et al. |
| 6,560,486 B1 | 5/2003 | Osorio et al. |
| 6,845,267 B2 | 1/2005 | Harrison et al. |
| 6,895,280 B2 | 5/2005 | Meadows et al. |
| 6,920,359 B2 | 7/2005 | Meadows et al. |
| 6,950,707 B2 | 9/2005 | Whitehurst |
| 6,993,384 B2 | 1/2006 | Bradley et al. |
| 7,004,948 B1 | 2/2006 | Pianca et al. |
| 7,107,097 B2 | 9/2006 | Stern et al. |
| 7,283,856 B2 | 10/2007 | Boling |
| 7,421,297 B2 | 9/2008 | Giftakis et al. |
| 7,548,775 B2 | 6/2009 | Kipke et al. |
| 2003/0139781 A1 | 7/2003 | Bradley et al. |
| 2004/0034394 A1* | 2/2004 | Woods et al. .......... 607/46 |
| 2004/0153129 A1 | 8/2004 | Pless et al. |
| 2004/0173221 A1 | 9/2004 | Singhal et al. |
| 2005/0004627 A1 | 1/2005 | Gibson et al. |
| 2005/0015128 A1 | 1/2005 | Rezai et al. |
| 2005/0075680 A1 | 4/2005 | Lowry et al. |
| 2005/0143790 A1 | 6/2005 | Kipke et al. |
| 2005/0143799 A1 | 6/2005 | Black et al. |
| 2005/0143800 A1 | 6/2005 | Lando et al. |
| 2005/0177039 A1 | 8/2005 | Mills |
| 2005/0222626 A1 | 10/2005 | DiLorenzo |
| 2005/0228249 A1 | 10/2005 | Boling |
| 2005/0267546 A1 | 12/2005 | Parramon et al. |
| 2006/0129203 A1 | 6/2006 | Garabedian et al. |
| 2006/0149336 A1 | 7/2006 | Meadows |
| 2006/0212093 A1* | 9/2006 | Pless et al. .......... 607/45 |
| 2006/0229686 A1 | 10/2006 | Giftakis et al. |
| 2006/0259079 A1 | 11/2006 | King |
| 2007/0032834 A1 | 2/2007 | Gliner et al. |
| 2007/0038250 A1 | 2/2007 | He et al. |
| 2007/0173902 A1 | 7/2007 | Maschino et al. |
| 2007/0225674 A1 | 9/2007 | Molnar et al. |
| 2008/0046035 A1 | 2/2008 | Fowler et al. |
| 2008/0172068 A1 | 7/2008 | Adams et al. |
| 2009/0082829 A1* | 3/2009 | Panken et al. .......... 607/45 |
| 2009/0118786 A1 | 5/2009 | Meadows et al. |
| 2009/0118787 A1 | 5/2009 | Moffitt et al. |
| 2009/0118804 A1 | 5/2009 | Moffitt et al. |
| 2009/0319004 A1* | 12/2009 | Sabel .......... 607/54 |

FOREIGN PATENT DOCUMENTS

| | | |
|---|---|---|
| WO | WO 9521591 A1 | 8/1995 |
| WO | WO 9843700 A1 | 10/1998 |
| WO | WO 2005061045 A1 | 7/2005 |
| WO | WO 2006105463 A2 | 10/2006 |

OTHER PUBLICATIONS

PCT Written Opinion of the International Search Authority for PCT/US2008/081848, Applicant: Boston Scientific Neuromodulation Corporation, Form PCT/ISA/237, dated Apr. 20, 2005 (10 pages).

Leuthardt, Eric C., et al., A brain-computer interface using electrocorticographic signals in humans, J. Neural Eng. 1 (2004) 63-71.

PCT International Preliminary Report on Patentability (Chapter I of the Patent Cooperation Treaty) for PCT/US2008/081848, Applicant: Boston Scientific Neuromodulation Corporation, Form PCT/IB/326 and 373, dated May 14, 2010 (9 pages).

* cited by examiner

FIG. 5

| Electrode Config. | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|
| 222 | 0 | 0 | -1 | 0 | 0 | 0 | 0 | 0 | 0 | 0 | 0.5 | 0.5 | 0 | 0 | 0 | 0 | 0 | 0 | 0 | 0 | 0 | 0 | 0 | 0 |
| 223 | 0 | 0 | -0.9 | 0 | 0 | 0 | -0.1 | 0 | 0 | 0 | 0.5 | 0.5 | 0 | 0 | 0 | 0 | 0 | 0 | 0 | 0 | 0 | 0 | 0 | 0 |
| 224 | 0 | 0 | -0.8 | 0 | 0 | 0 | -0.2 | 0 | 0 | 0 | 0.5 | 0.5 | 0 | 0 | 0 | 0 | 0 | 0 | 0 | 0 | 0 | 0 | 0 | 0 |
| 225 | 0 | 0 | -0.7 | 0 | 0 | 0 | -0.3 | 0 | 0 | 0 | 0.5 | 0.5 | 0 | 0 | 0 | 0 | 0 | 0 | 0 | 0 | 0 | 0 | 0 | 0 |
| 226 | 0 | 0 | -0.6 | 0 | 0 | 0 | -0.4 | 0 | 0 | 0 | 0.5 | 0.5 | 0 | 0 | 0 | 0 | 0 | 0 | 0 | 0 | 0 | 0 | 0 | 0 |
| 227 | 0 | 0 | -0.5 | 0 | 0 | 0 | -0.5 | 0 | 0 | 0 | 0.5 | 0.5 | 0 | 0 | 0 | 0 | 0 | 0 | 0 | 0 | 0 | 0 | 0 | 0 |
| 228 | 0 | 0 | -0.4 | 0 | 0 | 0 | -0.6 | 0 | 0 | 0 | 0.5 | 0.5 | 0 | 0 | 0 | 0 | 0 | 0 | 0 | 0 | 0 | 0 | 0 | 0 |
| 229 | 0 | 0 | -0.3 | 0 | 0 | 0 | -0.7 | 0 | 0 | 0 | 0.5 | 0.5 | 0 | 0 | 0 | 0 | 0 | 0 | 0 | 0 | 0 | 0 | 0 | 0 |
| 230 | 0 | 0 | -0.2 | 0 | 0 | 0 | -0.8 | 0 | 0 | 0 | 0.5 | 0.5 | 0 | 0 | 0 | 0 | 0 | 0 | 0 | 0 | 0 | 0 | 0 | 0 |
| 231 | 0 | 0 | -0.1 | 0 | 0 | 0 | -0.9 | 0 | 0 | 0 | 0.5 | 0.5 | 0 | 0 | 0 | 0 | 0 | 0 | 0 | 0 | 0 | 0 | 0 | 0 |
| 232 | 0 | 0 | 0 | 0 | 0 | 0 | -1 | 0 | 0 | 0 | 0.5 | 0.5 | 0 | 0 | 0 | 0 | 0 | 0 | 0 | 0 | 0 | 0 | 0 | 0 |
| 233 | 0 | 0 | 0 | 0 | 0 | 0 | -0.9 | 0 | 0 | 0 | 0.5 | 0.5 | 0 | 0 | -0.1 | 0 | 0 | 0 | 0 | 0 | 0 | 0 | 0 | 0 |
| 234 | 0 | 0 | 0 | 0 | 0 | 0 | -0.8 | 0 | 0 | 0 | 0.5 | 0.5 | 0 | 0 | -0.2 | 0 | 0 | 0 | 0 | 0 | 0 | 0 | 0 | 0 |
| 235 | 0 | 0 | 0 | 0 | 0 | 0 | -0.7 | 0 | 0 | 0 | 0.5 | 0.5 | 0 | 0 | -0.3 | 0 | 0 | 0 | 0 | 0 | 0 | 0 | 0 | 0 |
| 236 | 0 | 0 | 0 | 0 | 0 | 0 | -0.6 | 0 | 0 | 0 | 0.5 | 0.5 | 0 | 0 | -0.4 | 0 | 0 | 0 | 0 | 0 | 0 | 0 | 0 | 0 |
| 237 | 0 | 0 | 0 | 0 | 0 | 0 | -0.5 | 0 | 0 | 0 | 0.5 | 0.5 | 0 | 0 | -0.5 | 0 | 0 | 0 | 0 | 0 | 0 | 0 | 0 | 0 |
| 238 | 0 | 0 | 0 | 0 | 0 | 0 | -0.4 | 0 | 0 | 0 | 0.5 | 0.5 | 0 | 0 | -0.6 | 0 | 0 | 0 | 0 | 0 | 0 | 0 | 0 | 0 |
| 239 | 0 | 0 | 0 | 0 | 0 | 0 | -0.3 | 0 | 0 | 0 | 0.5 | 0.5 | 0 | 0 | -0.7 | 0 | 0 | 0 | 0 | 0 | 0 | 0 | 0 | 0 |
| 240 | 0 | 0 | 0 | 0 | 0 | 0 | -0.2 | 0 | 0 | 0 | 0.5 | 0.5 | 0 | 0 | -0.8 | 0 | 0 | 0 | 0 | 0 | 0 | 0 | 0 | 0 |
| 241 | 0 | 0 | 0 | 0 | 0 | 0 | -0.1 | 0 | 0 | 0 | 0.5 | 0.5 | 0 | 0 | -0.9 | 0 | 0 | 0 | 0 | 0 | 0 | 0 | 0 | 0 |
| 242 | 0 | 0 | 0 | 0 | 0 | 0 | 0 | 0 | 0 | 0 | 0.5 | 0.5 | 0 | 0 | -1 | 0 | 0 | 0 | 0 | 0 | 0 | 0 | 0 | 0 |
| 243 | 0 | 0 | 0 | 0 | 0 | 0 | 0 | 0 | 0 | 0 | 0.5 | 0.5 | 0 | 0 | -0.9 | 0 | 0 | 0 | -0.1 | 0 | 0 | 0 | 0 | 0 |
| 244 | 0 | 0 | 0 | 0 | 0 | 0 | 0 | 0 | 0 | 0 | 0.5 | 0.5 | 0 | 0 | -0.8 | 0 | 0 | 0 | -0.2 | 0 | 0 | 0 | 0 | 0 |
| 245 | 0 | 0 | 0 | 0 | 0 | 0 | 0 | 0 | 0 | 0 | 0.5 | 0.5 | 0 | 0 | -0.7 | 0 | 0 | 0 | -0.3 | 0 | 0 | 0 | 0 | 0 |
| 246 | 0 | 0 | 0 | 0 | 0 | 0 | 0 | 0 | 0 | 0 | 0.5 | 0.5 | 0 | 0 | -0.6 | 0 | 0 | 0 | -0.4 | 0 | 0 | 0 | 0 | 0 |
| 247 | 0 | 0 | 0 | 0 | 0 | 0 | 0 | 0 | 0 | 0 | 0.5 | 0.5 | 0 | 0 | -0.5 | 0 | 0 | 0 | -0.5 | 0 | 0 | 0 | 0 | 0 |
| 248 | 0 | 0 | 0 | 0 | 0 | 0 | 0 | 0 | 0 | 0 | 0.5 | 0.5 | 0 | 0 | -0.4 | 0 | 0 | 0 | -0.6 | 0 | 0 | 0 | 0 | 0 |
| 249 | 0 | 0 | 0 | 0 | 0 | 0 | 0 | 0 | 0 | 0 | 0.5 | 0.5 | 0 | 0 | -0.3 | 0 | 0 | 0 | -0.7 | 0 | 0 | 0 | 0 | 0 |
| 250 | 0 | 0 | 0 | 0 | 0 | 0 | 0 | 0 | 0 | 0 | 0.5 | 0.5 | 0 | 0 | -0.2 | 0 | 0 | 0 | -0.8 | 0 | 0 | 0 | 0 | 0 |
| 251 | 0 | 0 | 0 | 0 | 0 | 0 | 0 | 0 | 0 | 0 | 0.5 | 0.5 | 0 | 0 | -0.1 | 0 | 0 | 0 | -0.9 | 0 | 0 | 0 | 0 | 0 |
| 252 | 0 | 0 | 0 | 0 | 0 | 0 | 0 | 0 | 0 | 0 | 0.5 | 0.5 | 0 | 0 | 0 | 0 | 0 | 0 | -1 | 0 | 0 | 0 | 0 | 0 |
| 253 | 0 | 0 | 0 | 0 | 0 | 0 | 0 | 0 | 0 | 0 | 0.5 | 0.5 | 0 | 0 | 0 | 0 | 0 | 0 | -0.9 | 0 | 0 | 0 | -0.1 | 0 |
| 254 | 0 | 0 | 0 | 0 | 0 | 0 | 0 | 0 | 0 | 0 | 0.5 | 0.5 | 0 | 0 | 0 | 0 | 0 | 0 | -0.8 | 0 | 0 | 0 | -0.2 | 0 |
| 255 | 0 | 0 | 0 | 0 | 0 | 0 | 0 | 0 | 0 | 0 | 0.5 | 0.5 | 0 | 0 | 0 | 0 | 0 | 0 | -0.7 | 0 | 0 | 0 | -0.3 | 0 |
| 256 | 0 | 0 | 0 | 0 | 0 | 0 | 0 | 0 | 0 | 0 | 0.5 | 0.5 | 0 | 0 | 0 | 0 | 0 | 0 | -0.6 | 0 | 0 | 0 | -0.4 | 0 |
| 257 | 0 | 0 | 0 | 0 | 0 | 0 | 0 | 0 | 0 | 0 | 0.5 | 0.5 | 0 | 0 | 0 | 0 | 0 | 0 | -0.5 | 0 | 0 | 0 | -0.5 | 0 |
| 258 | 0 | 0 | 0 | 0 | 0 | 0 | 0 | 0 | 0 | 0 | 0.5 | 0.5 | 0 | 0 | 0 | 0 | 0 | 0 | -0.4 | 0 | 0 | 0 | -0.6 | 0 |
| 259 | 0 | 0 | 0 | 0 | 0 | 0 | 0 | 0 | 0 | 0 | 0.5 | 0.5 | 0 | 0 | 0 | 0 | 0 | 0 | -0.3 | 0 | 0 | 0 | -0.7 | 0 |
| 260 | 0 | 0 | 0 | 0 | 0 | 0 | 0 | 0 | 0 | 0 | 0.5 | 0.5 | 0 | 0 | 0 | 0 | 0 | 0 | -0.2 | 0 | 0 | 0 | -0.8 | 0 |
| 261 | 0 | 0 | 0 | 0 | 0 | 0 | 0 | 0 | 0 | 0 | 0.5 | 0.5 | 0 | 0 | 0 | 0 | 0 | 0 | -0.1 | 0 | 0 | 0 | -0.9 | 0 |
| 262 | 0 | 0 | 0 | 0 | 0 | 0 | 0 | 0 | 0 | 0 | 0.5 | 0.5 | 0 | 0 | 0 | 0 | 0 | 0 | 0 | 0 | 0 | 0 | -1 | 0 |

US 9,248,280 B2

CLOSED-LOOP FEEDBACK FOR STEERING STIMULATION ENERGY WITHIN TISSUE

FIELD OF THE INVENTION

The present inventions relate to the treatment of movement disorders, and more particularly, to deep brain stimulation (DBS) systems and methods.

BACKGROUND OF THE INVENTION

Implantable neurostimulation systems have proven therapeutic in a wide variety of diseases and disorders. For example, it is known to use such systems to treat neurological disorders, such as neurodegenerative diseases (e.g., Alzheimer's Disease, Parkinson's Disease, tremor, and epilepsy), brain ischemia, such as stroke, and limbic disorders, as well as non-neurological disorders, such as migraine headaches, obesity, and incontinence, by electrically stimulating selected portions of the brain. In a deep brain stimulation (DBS) procedure, typically used to treat Parkinson's Disease, Tremor, and Epilepsy, a selected deep brain structure, e.g., the anterior thalamus, ventrolateral thalamus (Thal), internal segment of globus pallidus (GPi), substantia nigra pars reticulata (SNr), subthalamic nucleus (STN), external segment of globus pallidus (GPe), and neostriatum, is electrically stimulated. Further details discussing the treatment of diseases using DBS are disclosed in U.S. Pat. Nos. 6,845,267, 6,845,267, and 6,950,707, which are expressly incorporated herein by reference. In a cortical brain stimulation procedure, typically used to rehabilitate stroke victims, but also providing benefits in the treatment of the other aforementioned disorders, the cortical brain tissue underneath the dura mater is electrically stimulated.

A typical implantable neurostimulation system used to electrically stimulate brain tissue includes electrodes, which are implanted at the desired stimulation site in the brain of the patient, and a neurostimulator implanted remotely from the stimulation site (e.g., in the chest region of the patient), but coupled either directly to the electrodes via one or more leads. The neurostimulation system may further comprise a handheld remote control (RC) to remotely instruct the neurostimulator to generate electrical stimulation pulses in accordance with selected stimulation parameters. The RC may, itself, be programmed by a technician attending the patient, for example, by using a Clinician's Programmer (CP), which typically includes a general purpose computer, such as a laptop, with a programming software package installed thereon.

Thus, in accordance with the stimulation parameters programmed by the RC and/or CP, electrical pulses can be delivered from the neurostimulator to the electrodes to stimulate or activate a volume of tissue and provide the desired efficacious therapy to the patient. The best stimulus parameter set will typically be one that delivers stimulation energy to the volume of tissue to be stimulated in order to provide the therapeutic benefit (e.g., treatment of movement disorders), while minimizing the volume of non-target tissue that is stimulated. A typical stimulation parameter set may include the electrodes that are acting as anodes or cathodes, as well as the amplitude, duration, and rate of the stimulation pulses.

When the neurostimulation system is implanted within a patient, a fitting procedure is typically performed to ensure that the stimulation leads and/or electrodes are properly implanted in effective locations of the patient, as well as to program the neurostimulator by selecting one or more effective sets of stimulation parameters that result in optimal treatment for the patient and/or optimal use of the stimulation resources. Notably, the persons that program the neurostimulators are often trained by experience alone, and lack formal training in the theory of neurostimulation. Thus, obtaining an optimal program is difficult and sometimes not achieved, resulting in a fitting process that is extremely time consuming and tedious.

Significantly, non-optimal electrode placement and stimulation parameter selections may result in excessive energy consumption due to stimulation that is set at too high an amplitude, too wide a pulse duration, or too fast a frequency; inadequate or marginalized treatment due to stimulation that is set at too low an amplitude, too narrow a pulse duration, or too slow a frequency; or stimulation of neighboring cell populations that may result in undesirable side effects. In addition, the brain is dynamic (e.g., due to disease progression, motor re-learning, or other changes), and a program (i.e., a set of stimulation parameters) that is useful for a period of time may not maintain its effectiveness and/or the expectations of the patient may increase. Thus, after the neurostimulation system has been implanted and fitted, the patient may have to schedule another visit to the physician in order to adjust the stimulation parameters of the neurostimulator if the treatment provided by the system is no longer effective or otherwise is not therapeutically or operationally optimum. All of these issues are poorly addressed by the present-day neurostimulation fitting techniques.

While neurostimulation systems have been disclosed that utilize a closed-loop method that involves sensing electrical signals within the brain of the patient and adjusting the electrical stimulation delivered to a target region within the brain of the patient (see, e.g., U.S. Pat. Nos. 5,683,422 and 6,016,449), the physician must still physically adjust the stimulation lead position in order to locate the locus of the delivered stimulation energy at the proper tissue site, and thereby achieve optimum, or otherwise effective, therapy. In addition, if the therapy provided by the implanted neurostimulation system no longer is optimum or effective, the patient may need to undergo another surgical procedure to adjust the physical position of the stimulation lead. Furthermore, it is often the case, either due to the dysfunction suffered by the patient or for other reasons, that the patient may have difficulty operating the RC to adjust the stimulation parameters to maintain optimum or effective treatment.

There, thus, remains a need for a neurostimulation system that can be more easily programmed to adjust the position of the locus of stimulation energy delivered by the system to brain tissue in order to optimize treatment of a patient suffering from a disease.

SUMMARY OF THE INVENTION

In accordance with a first aspect of the present inventions, a method of providing therapy to a patient is provided. The method comprises conveying electrical energy between electrodes to create a stimulation region in tissue adjacent the electrodes. The tissue may be, e.g., brain tissue, such as cortical brain tissue, although the stimulation of other tissue, such as spinal cord tissue, is contemplated by the present inventions in their broadest aspects. In one method, the patent suffers from a dysfunction, such as, e.g., a neurological disorder, in which case, the electrical energy may be conveyed between the electrodes to change the status of the dysfunction.

The method further comprises acquiring physiological information from the patient; for example, by sensing a non-cognitive based brain signal, a cognitive based brain signal, or a physiological end function, and analyzing the acquired physiological information. In the case where the electrical energy is conveyed between the electrodes to change the status of the dysfunction, the acquired physiological information may be indicative of the changed status of the dysfunction. In another method, the acquired physiological information is indicative of a desire of a patient to displace the locus of the stimulation region. The physiological information may be acquired by, e.g., sensing electrical signals at one or more of the electrodes or may be acquired by sensing electrical signals or other physiological parameters from devices other than the electrodes.

The method further comprises automatically displacing a locus of the stimulation region relative to the tissue based on the acquired physiological information. In one method, the locus of the stimulation region is displaced in response to a change in the acquired physiological information. The locus of the stimulation may be displaced in any one of a number of manners. For example, if the electrical energy is conveyed between the electrodes in accordance with a single timing channel to create the stimulation region, the locus of the stimulation region may be automatically displaced by modifying an electrode combination or by shifting electrical current between at least two of the electrodes for the single timing channel. If the electrical energy is conveyed between the electrodes in accordance with a plurality of timing channels to create the stimulation region, the locus of the stimulation region may be automatically displaced by modifying the relative magnitude of the electrical energy conveyed in accordance with the timing channels.

In accordance with a second aspect of the present inventions, a neurostimulation system is provided. The neurostimulation system comprises a plurality of electrical terminals configured for being electrically coupled to a plurality of electrodes, and output stimulation circuitry configured for conveying electrical energy between the electrical terminals, thereby creating a stimulation region in tissue of a patient when the electrodes are located adjacent the tissue, and monitoring circuitry configured for acquiring physiological information from a patient.

In one embodiment, the output stimulation circuitry is configured for conveying the electrical energy between the electrical terminals to change the status of a dysfunction suffered by the patient, and the acquired physiological information is indicative of the changed status of the dysfunction. In another embodiment, the acquired physiological information is indicative of a desire of the patient to displace the locus of the stimulation region. The monitoring circuitry may be configured for acquiring the physiological information by sensing electrical signals at the electrodes, although the monitoring circuitry may alternatively be configured for acquiring the physiological information by other means. The monitoring circuitry may be configured for acquiring the physiological information by, e.g., sensing a non-cognitive based brain signal, a cognitive based brain signal, or a physiological end-function.

The neurostimulation system further comprises control circuitry configured for analyzing the acquired physiological information from the monitoring circuitry and for controlling the output stimulation circuitry to displace a locus of the stimulation region relative to the tissue based on the analysis of the acquired physiological information. In one embodiment, the control circuitry is configured for automatically controlling the output stimulation circuitry to displace the locus of the stimulation region in response to a change in the acquired physiological information. The control circuitry may be configured for controlling the output stimulation circuitry to displace locus of the stimulation in any one of a number of manners.

For example, if the output stimulation circuitry is configured for conveying the electrical energy between the electrodes in accordance with a single timing channel to create the stimulation region, the control circuitry may be configured for controlling the output stimulation circuitry to displace the locus of the stimulation region by modifying an electrode combination for the single timing channel, or the control circuitry may be configured for controlling the output stimulation circuitry to displace the locus of the stimulation region by shifting electrical current between at least two of the electrodes for the single timing channel. If the output stimulation circuitry is configured for conveying the electrical energy between the electrodes in accordance with a plurality of timing channels to create the stimulation region, the control circuitry may be configured for controlling the output stimulation circuitry to displace the locus of the stimulation region by modifying the relative magnitude of the electrical energy conveyed in accordance with the timing channels.

In one embodiment, the neurostimulation system further comprises a case, and the electrical terminals and output stimulation circuitry are contained in the case to form a neurostimulator, which may be implantable. The monitoring circuitry and/or control circuitry may also be contained in the case, although in other embodiments, the monitoring circuitry and/or control circuitry may be separate from the neurostimulator.

In accordance with a third aspect of the present inventions, an external programmer for a neurostimulator is provided. The neurostimulator is coupled to an array of electrodes between which electrical energy may be conveyed to create a stimulation region within tissue of a patient. The external programmer comprises input circuitry configured for receiving physiological information from a patient. In one embodiment, the acquired physiological information is indicative of a changed status of a dysfunction suffered by the patient. In another embodiment, the acquired physiological information is indicative of a desire of the patient to displace the locus of the stimulation region.

The external programmer further comprises processing circuitry configured for analyzing the physiological information and automatically generating a series of stimulation parameter sets based on the analysis of the physiological information. In one embodiment, the processing circuitry is configured for generating the stimulation parameter sets in response to changes in the acquired physiological information. The stimulation parameter sets correspond to different loci of the stimulation region relative to the tissue. In one embodiment, the stimulation parameter sets define different electrode combinations or different magnitudes for the electrical current at the same electrode for a single timing channel. In another embodiment, the stimulation parameter sets define different magnitudes for the electrical energy conveyed between the electrodes for one of a plurality of different timing channels. The external programmer further comprises output circuitry (e.g., telemetry circuitry) configured for transmitting the series of stimulation parameter sets to the neurostimulator.

In accordance with a fourth aspect of the present inventions, a method of providing therapy to a patient is provided. The method comprises delivering electrical energy to tissue (e.g., brain tissue, such as cortical brain tissue) of the patient in accordance with one or more stimulation parameters (e.g., at least one of an electrode combination, a pulse amplitude, a pulse duration, and a pulse rate). In one method, the patient suffers from a dysfunction (e.g., a neurological disorder), and the electrical energy is delivered to the tissue to change the status of the dysfunction. The method further comprises sensing a cognitive brain signal (e.g., one that is indicative of a desire of the patient to change the stimulation parameter(s)). In one method, the electrical energy is delivered from one or more electrodes to the tissue, and the cognitive brain signal is sensed by the one or more electrodes. The method further comprises analyzing the cognitive brain signal (e.g., at least one of a µ rhythm, β rhythm, γ rhythm), and modifying the stimulation parameter(s) based on the analysis of the cognitive brain signal. In one method, the electrical energy creates a stimulation region within the tissue, and the stimulation parameter(s) are modified to electronically displace the stimulation region relative to the tissue.

In accordance with a fifth aspect of the present inventions, a neurostimulation system is provided. The neurostimulation system comprises a plurality of electrical terminals configured for being electrically coupled to a plurality of electrodes. The neurostimulation system further comprises output stimulation circuitry configured for conveying electrical energy to the electrodes in accordance with one or more stimulation parameters (e.g., at least one of an electrode combination, a pulse amplitude, a pulse duration, and a pulse rate). In one embodiment, the output stimulation circuitry is configured for conveying the electrical energy to the electrodes to change the status of a dysfunction suffered by the patient. The neurostimulation system further comprises monitoring circuitry configured for sensing a cognitive brain signal (e.g., one that is indicative of a desire of the patient to change the stimulation parameter(s)). In one embodiment, the monitoring circuitry is configured for sensing the cognitive brain signal via the electrodes.

The neurostimulation system further comprises control circuitry configured for analyzing the sensed cognitive brain signal (e.g., at least one of a µ rhythm, β rhythm, γ rhythm) and for modifying the stimulation parameter(s) based on the analysis of the sensed cognitive brain signal. In one embodiment, the output stimulation circuitry is configured for conveying electrical energy to the electrodes to create a stimulation region within tissue, and the control circuitry is configured for modifying the stimulation parameter(s) to electronically displace the stimulation region relative to the tissue. In another embodiment, the system comprises a case, in which case, the electrical terminals and output stimulation circuitry, monitoring circuitry, and/or control circuitry may be contained in the case to form a neurostimulator (e.g., an implantable neurostimulator).

In accordance with a sixth aspect of the present inventions, an external programmer for a neurostimulator is provided. The external programmer comprises input circuitry configured for receiving a cognitive brain signal from a patient, and processing circuitry configured for analyzing the cognitive brain signal and automatically generating a stimulation parameter set (e.g., at least one of an electrode combination, a pulse amplitude, a pulse duration, and a pulse rate) based on the analysis of the cognitive brain signal (e.g., at least one of a µ rhythm, β rhythm, γ rhythm). In one embodiment, the cognitive brain signal is indicative of a desire of the patient. The external programmer further comprises output circuitry (e.g., telemetry circuitry) configured for transmitting the stimulation parameter set to the neurostimulator.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 5 is a current steering navigation table that can be used to electronically displace the stimulation region within the electrode array using the technique of FIGS. 4A-4E;

DETAILED DESCRIPTION OF THE EMBODIMENTS

At the outset, it is noted that the description that follows relates to a cortical brain stimulation system. However, it is to be understood that, while the invention lends itself well to applications in cortical brain stimulation, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a deep brain stimulator, a spinal cord stimulator, peripheral nerve stimulator, microstimulator, or in any other neural stimulator configured to treat urinary incontinence, sleep apnea, shoulder sublaxation, headache, etc.

Figure 1:
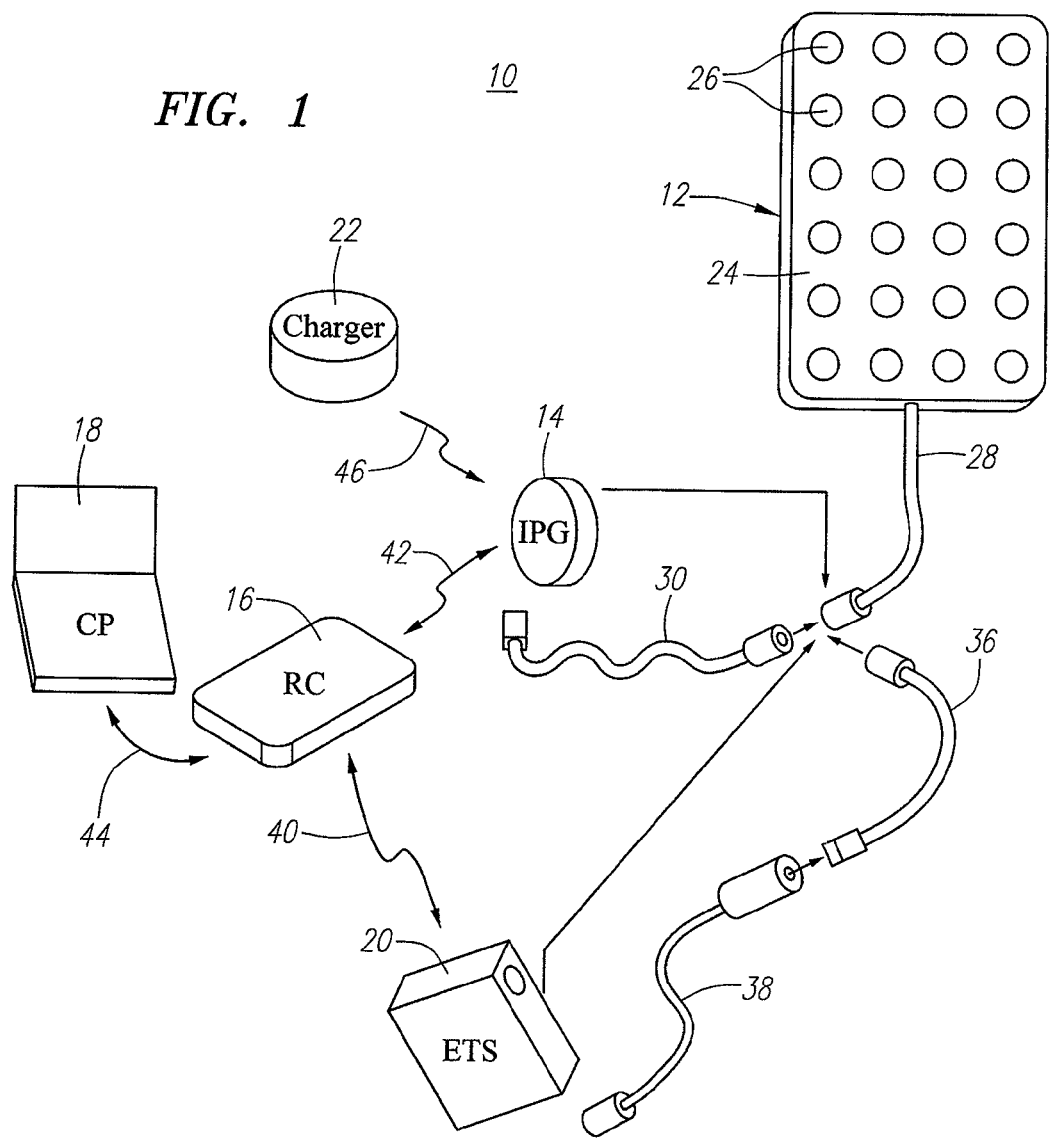
FIG. 1 is a plan view of a brain stimulation system constructed in accordance with one embodiment of the present inventions.
Figure 2:
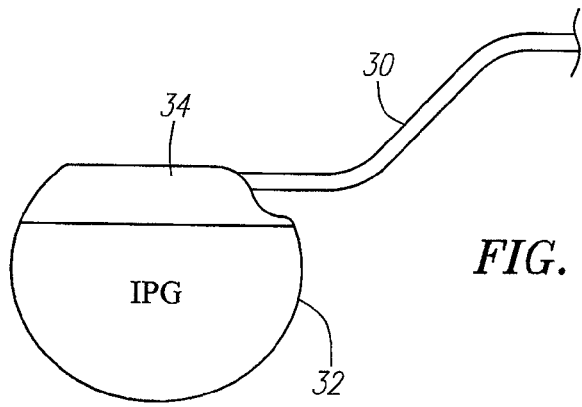
FIG. 2 is a side view of an implantable pulse generator (IPG) used in the brain stimulation system of FIG. 1.

Turning first to FIG. 1, an exemplary brain stimulation system 10 generally includes an electrode array 12, an implantable pulse generator (IPG) 14, an external remote controller RC 16, a clinician's programmer (CP) 18, an External Trial Stimulator (ETS) 20, and an external charger 22. In the illustrated embodiment, the brain stimulation system 10 is designed to treat a dysfunction suffered by the patient is a neurological disorder, such as a neurodegenerative disease (e.g., Alzheimer's Disease, Parkinson's Disease, tremor, and epilepsy) or brain ischemia, such as stroke, and limbic disorders, or a non-neurological disorder, such as a migraine headache, obesity, or incontinence, by electrically stimulating selected portions of the brain.

The electrode array 12 comprises a planar membrane 24 and a plurality of electrodes 26 arranged on the planar membrane 24 as a two-dimensional grid that is sized to cover a surface of at least a portion of the cortex of a patient's brain. The electrode array 12 may have a suitable number of electrodes 26 (e.g., 24, 36, 48, or 64 electrodes) and may have a suitable electrode spacing (e.g., 1 cm or 1 mm). The actual number and spacing of the electrodes 26 will, of course, vary according to the intended application. The electrode array 12 further comprises a lead 28 electrically connected to the electrodes 26. In alternative embodiments, the electrode array 12 may take the form of a stimulation lead designed to be introduced through a burr hole in the cranium of the patient and then arranged in a two-dimensional patterns, such as, e.g., the stimulation leads described in U.S. patent application Ser. No. 11/010,232, which is expressly incorporated herein by reference, or may be carried by a deep brain stimulation lead.

The IPG 14 may be directly coupled to the electrode array 12 or indirectly coupled to the electrode array 12 via a percutaneous lead extension 30. As will be described in further detail below, the IPG 14 receives physiological information sensed by the electrode array 12 and, based on this sensed physiological information, delivers electrical stimulation energy in the form of a pulsed electrical waveform (i.e., a temporal series of electrical pulses) to the electrode array 12 in accordance with a set of stimulation parameters. The IPG 14 comprises an outer case 32 for housing the electronic and other components (described in further detail below), and a connector 34 to which the proximal end of the percutaneous lead extension 30 mates in a manner that electrically couples the electrodes 26 to the electronics within the outer case 32. The outer case 32 is composed of an electrically conductive, biocompatible material, such as titanium, and forms a hermetically sealed compartment wherein the internal electronics are protected from the body tissue and fluids. In some cases, the outer case 32 may serve as an electrode.

The ETS 20 may also be directed coupled to the electrode array 12 or indirectly coupled to the electrode array 12 via a percutaneous lead extension 36 and external cable 38. The ETS 20, which has similar pulse generation circuitry as the IPG 14, also delivers electrical stimulation energy in the form of a pulse electrical waveform to the electrodes 26 accordance with a set of stimulation parameters and receives sensed physiological information from the electrodes 26. The major difference between the ETS 20 and the IPG 14 is that the ETS 20 is a non-implantable device that is used on a trial basis after the electrode array 12 has been implanted and prior to implantation of the IPG 14, to test the responsiveness of the stimulation that is to be provided. Further details of an exemplary ETS are described in U.S. Pat. No. 6,895,280, which is expressly incorporated herein by reference.

The RC 16 may be used to telemetrically control the ETS 20 via a bi-directional RF communications link 40. Once the IPG 14 and electrode array 12 are implanted, the RC 16 may be used to telemetrically control the IPG 14 via a bi-directional RF communications link 42. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. The details of the RC 16 will be described in further detail below.

The CP 18 provides clinician detailed stimulation parameters for programming the IPG 14 and ETS 20 in the operating room and in follow-up sessions. The CP 18 may perform this function by indirectly communicating with the IPG 14 or ETS 20, through the RC 16, via an IR communications link 44. Alternatively, the CP 18 may directly communicate with the IPG 14 or ETS 20 via an RF communications link (not shown). Further details discussing the CP 18 will be described in further detail below.

The external charger 22 is a portable device used to transcutaneously charge the IPG 14 via an inductive link 48. Once the IPG 14 has been programmed, and its power source has been charged by the external charger 22 or otherwise replenished, the IPG 14 may function as programmed without the RC 16 or CP 18 being present. For purposes of brevity, the details of the external charger 22 will not be described herein. Details of exemplary embodiments of external chargers are disclosed in U.S. Pat. No. 6,895,280, which has been previously incorporated herein by reference.

As briefly discussed above, the IPG 14 includes pulse generation circuitry that conveys the electrical stimulation energy in the form of a pulsed electrical waveform between the electrodes (the electrodes 26 and the IPG case) in accordance with a set of stimulation parameters, thereby delivering electrical energy to the tissue adjacent the electrodes 26. As a result, the status of the dysfunction suffered by the patient will change, and optimally will be improved. Such stimulation parameters may comprise electrode combinations, which define the electrodes that are activated as anodes (positive), cathodes (negative), and turned off (zero), and electrical pulse parameters, which define the pulse amplitude (measured in milliamps or volts depending on whether the IPG 14 supplies constant current or constant voltage to the electrodes 26), pulse duration (measured in microseconds), and pulse rate (measured in pulses per second). As will be described in further detail below, the electrical energy may be conveyed between the electrodes in accordance with a single time channel or multiple timing channels.

Electrical stimulation will occur between two (or more) activated electrodes, one of which may be the IPG case. Simulation energy may be transmitted to the tissue in a monopolar or multipolar (e.g., bipolar, tripolar, etc.) fashion. Monopolar stimulation occurs when a selected one of the array electrodes 26 is activated along with the case of the IPG 14, so that stimulation energy is transmitted between the selected electrode 26 and case. Bipolar stimulation occurs when two of the array electrodes 26 are activated as anode and cathode, so that stimulation energy is transmitted between the selected electrodes 26. Tripolar stimulation occurs when three of the array electrodes 26 are activated, two as anodes and the remaining one as a cathode, or two as cathodes and the remaining one as an anode.

As briefly discussed above, sensed physiological information is used to modify the stimulation parameters in accordance with which the IPG 14 delivers electrical energy between the electrodes 26 (including the case 32). In the preferred embodiment, the physiological information is sensed by the electrodes 26 and received by the IPG 14, although in alternative embodiments, the physiological information may be sensed by sensors other than the electrodes 26 and may be received by devices other than the IPG 16. In any event, the stimulation parameters are automatically adjusted in a manner that electronically displaces the locus of a stimulation region created by the electrical energy in the tissue. Preferably, the stimulation region is displaced in a manner that optimizes or more effectively treats the dysfunction of the patient.

In one embodiment, the sensed physiological information is indicative of the changed status of the dysfunction resulting from the delivery of the electrical stimulation energy to the tissue, in which case, the stimulation parameters may be automatically adjusted by formulating a cost function and using an optimization algorithm (e.g., derivative-based, genetic algorithm, stimulated-annealing, etc.) that operates on the cost function and the sensed physiological information as an input.

In the illustrated embodiment, the sensed physiological information that is indicative of the changed status of the dysfunction may be obtained from electrical brain signals, and in particular, non-cognitive based neural signals, such as electroencephalographic (EEG) or electrocorticographic (ECoG) signals obtained from portions of the brain that can be correlated to the dysfunction. In this case, the electrode array 12, which can be sub-durally placed adjacent the cortex of the brain, can sense the brain signals in the cortical region of the brain. Alternatively, a separate array of electrodes may be located on top of the patient's scalp to measure the brain signals, although the resolution and clarity of the brain signals may not be as good as if the brain signals were measured closer to the brain. Further details discussing the sensing of cortical brain electrical activity are disclosed in U.S. Pat. No. 6,016,449, which is expressly incorporated herein by reference.

In an alternative embodiment, the brain signals are sensed in the deep brain regions of the patient, e.g., the thalamus, basal ganglia, hypothalamus, or any other region where the electrical activity reflects the dysfunction (e.g., motor dysfunction or mood/psychololgical disorder). In this case, one or more deep brain stimulation leads can be implanted within the brain to sense the deep brain electrical activity. In another alternative embodiment, chemicals, rather than electrical brain signals, are sensed. For example, an electrochemical sensor (not shown) can be used to sense the amount of glutamate present in a deep brain region, such as the subthalamic nucleus or the substantia nigra. The level of the glutamate is an indication of the relative activity of the brain region in which the glutamate is present. Further details discussing the sensing of deep brain electrical activity and other deep brain information are disclosed in U.S. Pat. No. 5,683,422, which is expressly incorporated herein by reference.

In another alternative embodiment, a separate patient monitor may be used to sense physiological information from a source other than the brain. For example, physiological end-function information, such as muscle spasticity (tremor) or muscle limitations (bradykinesia or rigidity), can be measured using quantitative motor assessment systems. Physiological information, such as neuromuscular torque and power, can be measured using isokinetic dynamometers. Physiological information, such as balance, can be measured using balance testing devices. Physiological information, such as posture, balance, motor control, and gait, can be measured using motion tracking systems. Physiological information, such as joint flexion/extension, can be measured using goniometers. Although the above-described physiological information is typical of information indicative of motor dysfunctions, such as those caused by Parkinson's Disease, epilepsy, and tremor, physiological information that indicates a status of other dysfunctions can be measured. Further details discussing the acquisition of physiological end-function information is described in U.S. patent application Ser. No. 11/934,731, which is expressly incorporated herein by reference.

In another embodiment, rather than, or in addition to, the sensed physiological information being indicative of the changed status of the dysfunction, the physiological information may be indicative of the patient's intention to displace the locus of the stimulation region, in which case, the stimulation parameters may be automatically adjusted by correlating the characteristics of the sensed physiological information with the intentions of the patient using an appropriate training approach (e.g., using a neural network). In the illustrated embodiment, the sensed physiological information that is indicative of the patient's intentions is obtained from electrical brain signals, and in particular, cognitive based neural signals, such as EEG or ECoG signals obtained from brain regions that can be correlated to the patient's intentions, such as the pre-frontal, pre-motor, sensorimotor, and speech processing cortical areas, or cortical areas controlling imagery of certain actions. These brain signals may be sensed by the electrode array 12 sub-durally placed adjacent the cortex of the brain, or may be sensed by a separate array of electrodes located on top of the patient's scalp to measure the brain signals, to form a brain-computer interface (BCI).

A candidate processing paradigm may including identifying changes in amplitude in the components of the spectrum of the sensed brain signals; for example, the $\mu$, $\beta$, and $\gamma$ rhythms, with the latter rhythm being highly correlative to the imagery of joystick movements. Several training sessions can be performed to correlate the characteristics of a selected rhythm with a particular imagined movement, such as up, down, left, or right. Thus, the brain signals of a patient can be analyzed to determine the intentions of the patient simply by the patient imagining certain movements. It can be appreciated that this embodiment allows a patient with severe motor disabilities, or who is otherwise incapable of adjusting the stimulation parameters of the stimulation energy provided to the patient, to electronically displace the locus of the stimulation region created by the stimulation energy simply by imagining it. Further details discussing the use of BCIs are disclosed in Eric C. Leuthardt, et al., A Brain-Computer Interface Using Electrocorticograpic Signals in Humans, J. Neural Eng. 1 (2004) 63-71.

The locus of the stimulation region may be electronically displaced in any one of a variety of manners.

In one method, different electrode combinations can be discretely selected to change the locus of the stimulation region from one location to another location within the electrode array 12. For example, and with reference to FIG. 3A, the electrode array 12 may comprise a first stimulating group of electrodes having one electrode in the third row (electrode E11) set to a "+" polarity (i.e., as an anode) and another electrode in the fourth row (electrode E15) set to a "−" polarity (i.e., as a cathode). This polarity and grouping initially causes electrical current to flow from electrode E11 to electrode E15 in a bipolar fashion, which results in a single stimulation region 46 between electrodes E11 and E15.

Figure 3B:
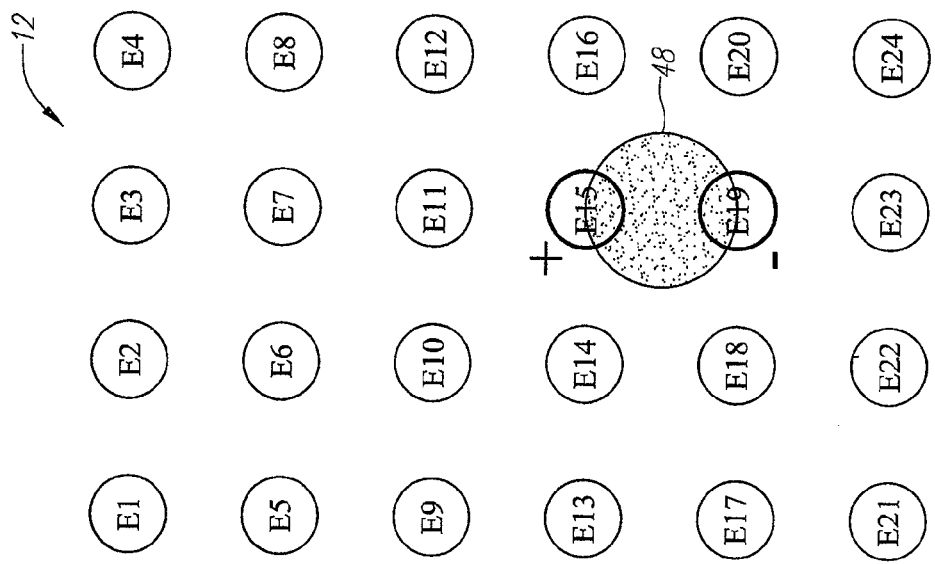
FIGS. 3A-3E are plan views showing one technique for electronically displacing a stimulation region within an electrode array used in the brain stimulation system of FIG. 1.
Figure 3A:
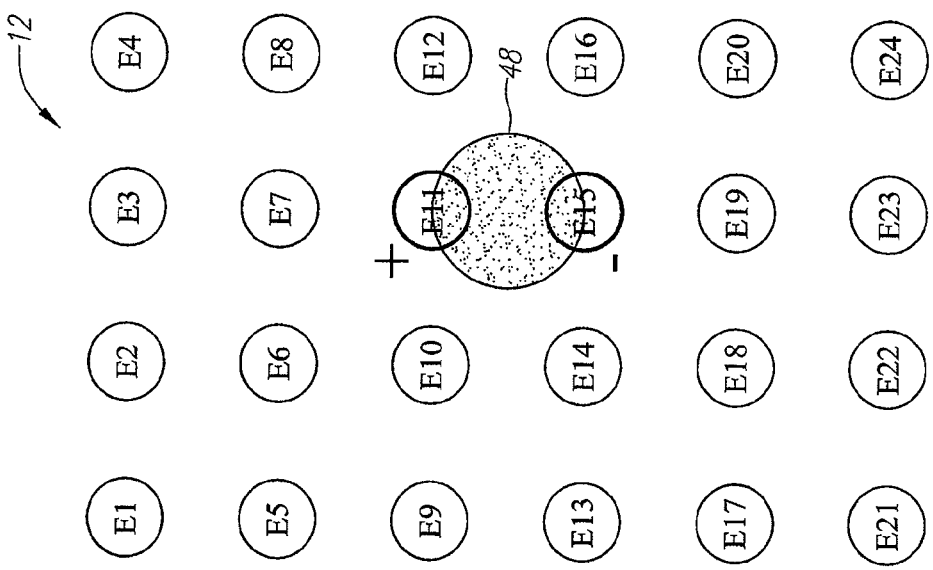

The stimulation region 48 can be electronically displaced down the tissue from its initial position by selecting a second stimulating group of electrodes comprising one electrode in the fourth row (electrode E15) set to a "+" polarity (i.e., as an anode) and another electrode in the fifth row (electrode E19) set to a "−" polarity (i.e., as a cathode), as shown in FIG. 3B. This polarity and grouping causes electrical current to flow from electrode E15 to electrode E19 in a bipolar fashion, which results in the location of the single stimulation region 48 between electrodes E15 and E19.

Figures 3C, 3D:
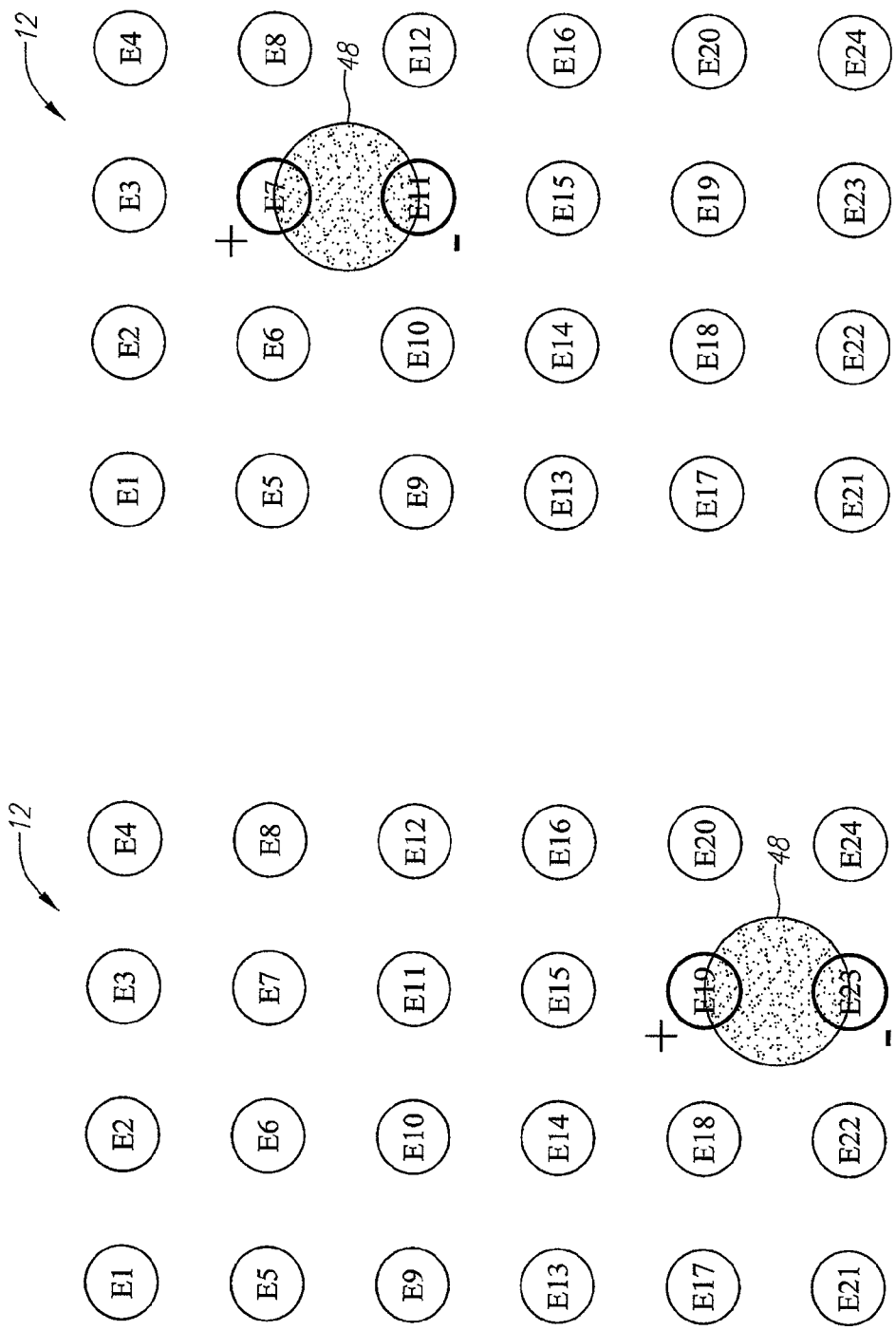

The stimulation region 48 can be electronically displaced down the tissue by, selecting a third stimulating group of electrodes comprising one electrode in the fifth row (electrode E19) set to a "+" polarity (i.e., as an anode) and another electrode in the fifth row (electrode E23) set to a "−" polarity (i.e., as a cathode), as shown in FIG. 3C. This polarity and grouping causes electrical current to flow from electrode E19 to electrode E23 in a bipolar fashion, which results in the location of the single stimulation region 48 between electrodes E19 and E23.

The stimulation region 48 can be electronically displaced up the tissue from its initial position by, e.g., selecting a fourth stimulating group of electrodes comprising one electrode in the second row (electrode E7) set to a "+" polarity (i.e., as an anode) and another electrode in the third row (electrode E11) set to a "−" polarity (i.e., as a cathode), as shown in FIG. 3D. This polarity and grouping causes electrical current to flow from electrode E7 to electrode E11 in a bipolar fashion, which results in the location of the single stimulation region 48 between electrodes E7 and E11.

Figures 3E, 4A:
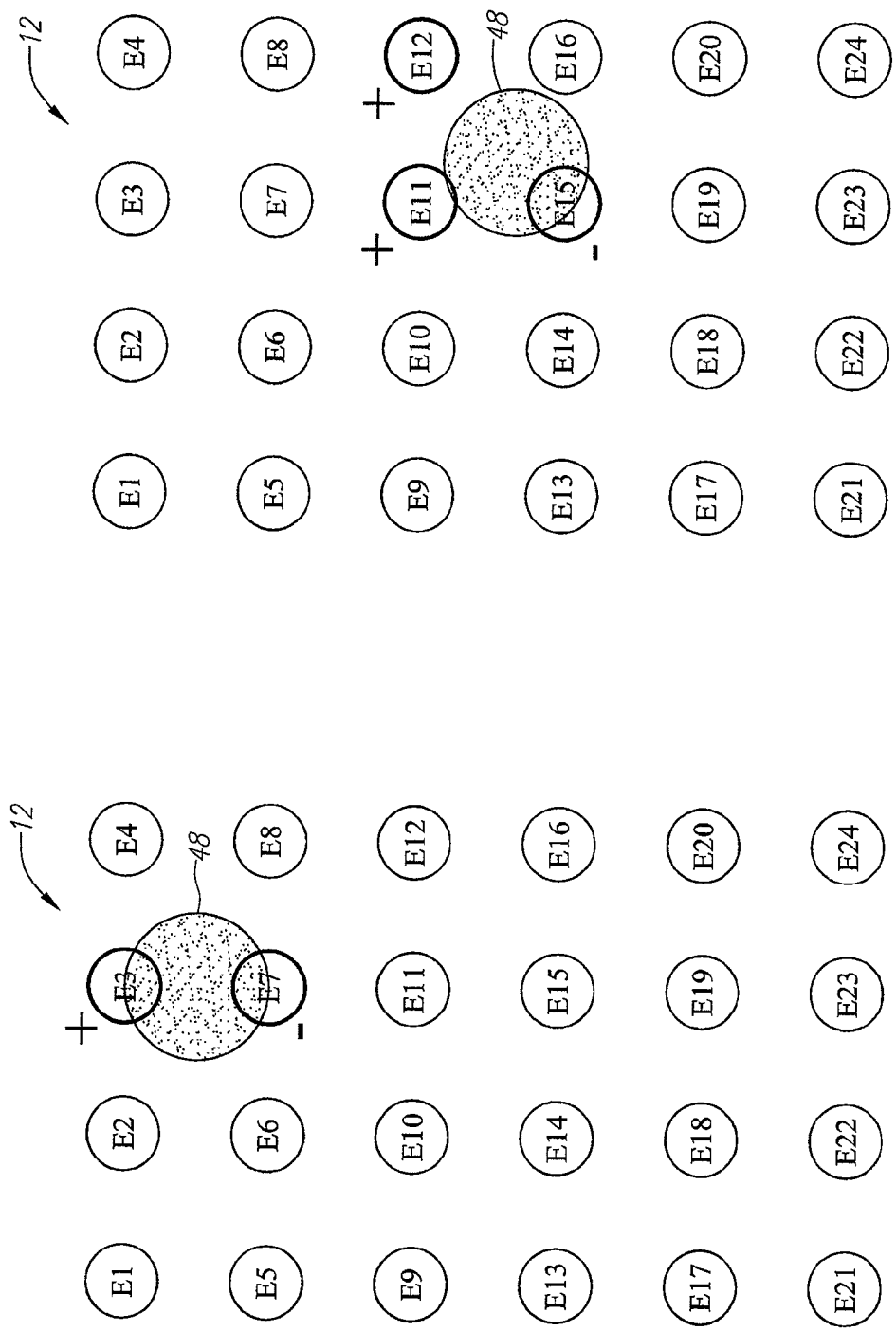
FIGS. 4A-4E are plan views showing another technique for electronically displacing a stimulation region within the electrode array.

The stimulation region 48 can be electronically displaced down the tissue by, selecting a fifth stimulating group of electrodes comprising one electrode in the first row (electrode E3) set to a "+" polarity (i.e., as an anode) and another electrode in the second row (electrode E7) set to a "−" polarity (i.e., as a cathode), as shown in FIG. 3E. This polarity and grouping causes electrical current to flow from electrode E3 to electrode E7 in a bipolar fashion, which results in the location of the single stimulation region 48 between electrodes E3 and E7.

Of course, other electrode combinations, including monopolar and tripolar combinations, can be selected to electronically displace the locus of the stimulation region up or down the tissue or in any other direction, including left, right, and even diagonal.

In another method, rather than discretely selecting different combinations of electrodes, electrical current can be gradually "steered" or shifted between electrodes to electronically displace the locus of the stimulation region. For example, referring to FIG. 4A, the electrode array 12 may initially have a tripolar stimulating group of electrodes having two electrodes in the third row (electrodes E11 and E12) set to a "+" polarity (i.e., as anodes), and one electrode in the fourth row (electrode E15) set to a "−" polarity (i.e., as a cathode). This polarity and grouping initially causes electrical current to flow from electrodes E11, E12 to electrode E15 in a bipolar fashion, which results in a single stimulation region 48 adjacent electrode E15 between the third and fourth rows of electrodes. Assuming that the stimulating group of electrodes is assigned a "group amplitude," which is the absolute value total for all of the cathodes (− electrodes) in a single stimulating group, the default fractionalized electrical current for such group might be 100% on the cathode (i.e., electrode E15) and 50% on each anode (i.e., electrodes E11, E12). The stimulation region 48 can be displaced relative to the tissue by shifting electrical current between electrodes.

Figures 4B, 4C:
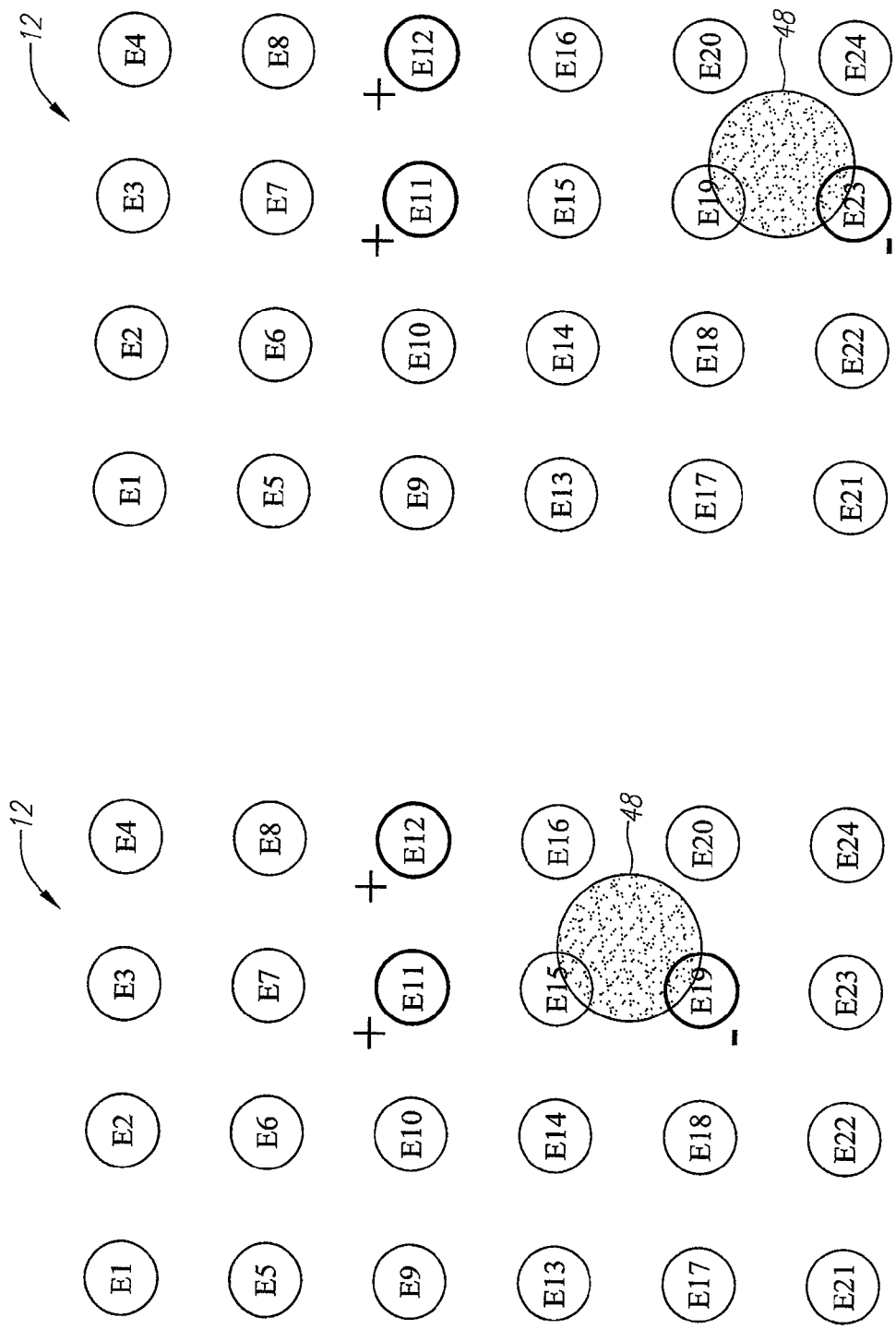

For example, the stimulation region 48 can be displaced down the tissue by gradually including electrode E19 within the stimulating electrode group and gradually excluding electrode E15 from the stimulating electrode group (in effect, creating a quadpolar electrode arrangement). That is, the fractionalized cathodic current flowing through electrode E19 is increased toward 100%, while the fractionalized cathodic current flowing through electrode E15 is decreased toward 0%. As a result, the stimulation region 48 moves from its initial position adjacent electrode E15 to a position adjacent electrode E19, as shown in FIG. 4B. In one embodiment, a current steering table can be utilized to gradually shift current between electrodes. For example, FIG. 5 illustrates a portion of one exemplary steering table containing a series of stimulation parameter sets, where the fractionalized cathodic current is shifted from electrode E15 to electrode E19 in 10% steps. Thus, to shift the cathodic current over the fractionalized cathodic current range of 100%/0% and 0%/100% for the electrodes E15, E19, the steering table may be stepped through beginning with row 542 and ending with row 552.

The stimulation region 48 can be further displaced down the tissue by gradually including electrode E23 within the stimulating electrode group and gradually excluding electrode E19 from the stimulating electrode group in the same manner. That is, the fractionalized cathodic current flowing through electrode E23 is increased toward 100%, while the fractionalized cathodic current flowing through electrode E19 is decreased toward 0%. As a result, the stimulation region 48 moves from its initial position adjacent electrode E19 to a position adjacent electrode E23, as shown in FIG. 4C. To shift the cathodic current over the fractionalized cathodic current range of 100%/0% and 0%/100% for the electrodes E19, E23, the steering table illustrated in FIG. 5 may be stepped through beginning with row 552 and ending with row 562.

Figures 4D, 4E:
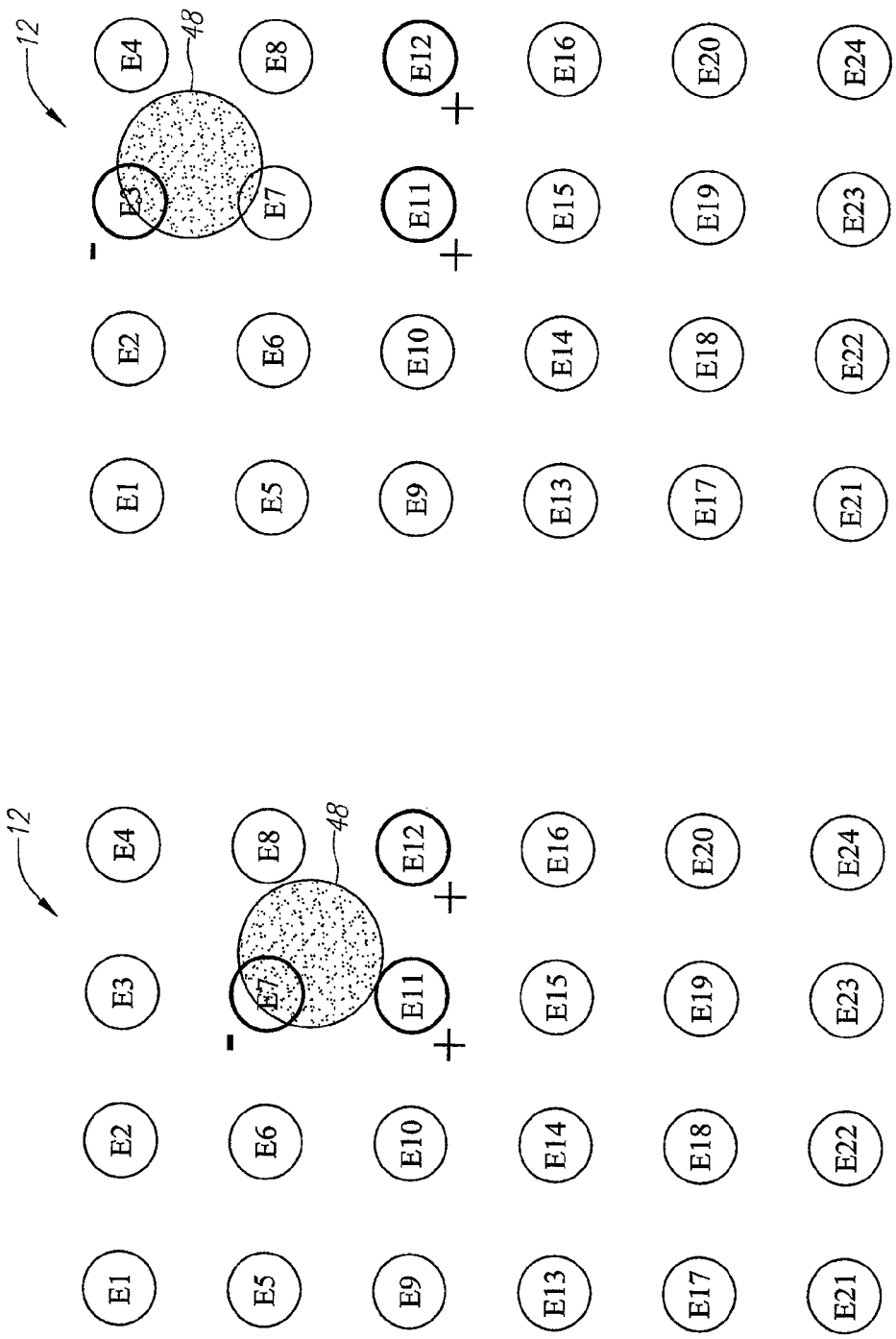

The stimulation region 48 can likewise be displaced up the tissue by gradually including electrode E7 within the stimulating electrode group and gradually excluding electrode E15 from the stimulating electrode group. That is, the fractionalized current flowing through electrode E7 is increased toward 100%, while the fractionalized current flowing through electrode E15 is decreased toward 0%. As a result, the stimulation region 48 moves from its initial position adjacent electrode E15 to a position adjacent electrode E7, as shown in FIG. 4D. To shift the cathodic current over the fractionalized cathodic current range of 100%/0% and 0%/100% for the electrodes E15, E7, the steering table illustrated in FIG. 5 may be stepped through beginning with row 542 and ending with row 532.

The stimulation region 48 can be further displaced down the tissue by gradually including electrode E3 within the stimulating electrode group and gradually excluding electrode E7 from the stimulating electrode group in the same manner. That is, the fractionalized cathodic current flowing through electrode E3 is increased toward 100%, while the fractionalized cathodic current flowing through electrode E7 is decreased toward 0%. As a result, the stimulation region 48 moves from its position adjacent electrode E7 to a position adjacent electrode E3, as shown in FIG. 4E. To shift the cathodic current over the fractionalized cathodic current range of 100%/0% and 0%/100% for the electrodes E7, E3, the steering table illustrated in FIG. 5 may be stepped through beginning with row 532 and ending with row 522.

Of course, the electrical current can be shifted between two or more electrodes of other electrode combinations, including monopolar combinations (e.g., shifting anodic current between two electrodes), to electronically displace the locus of the stimulation region up or down the tissue or in any other direction, including left, right, and even diagonal. It should be appreciated that although a steering table (as a look-up table) has been described herein as being used to shift current between cathodes or anodes, current shifting can be effecting using other means, such as analytical equations, formulas, and algorithms.

Figure 6A:
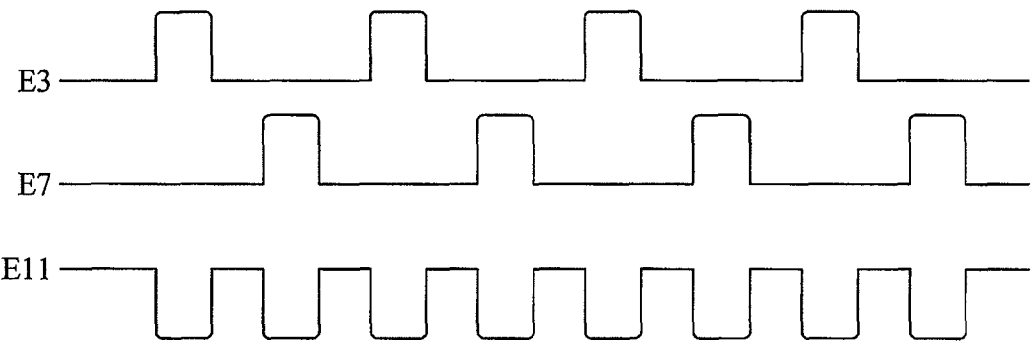
FIGS. 6A-6C are timing diagrams that can be used to electronically displace a stimulation region within an electrode array using multiple timing channels.
Figure 7B:
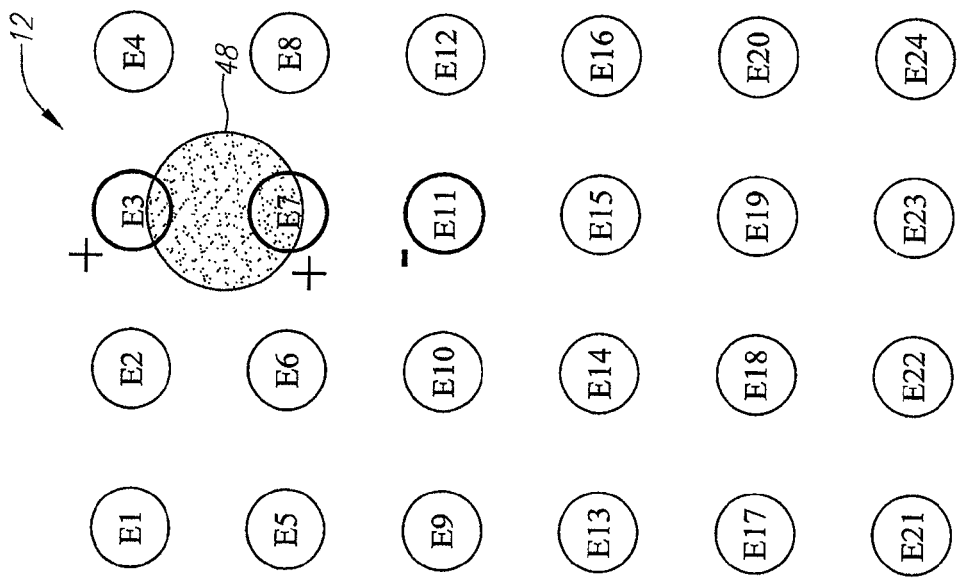
FIGS. 7A-7C are plan views showing another technique for electronically displacing a stimulation region within the electrode array in accordance with the timing channels of FIGS. 6A-6C.
Figure 7A:
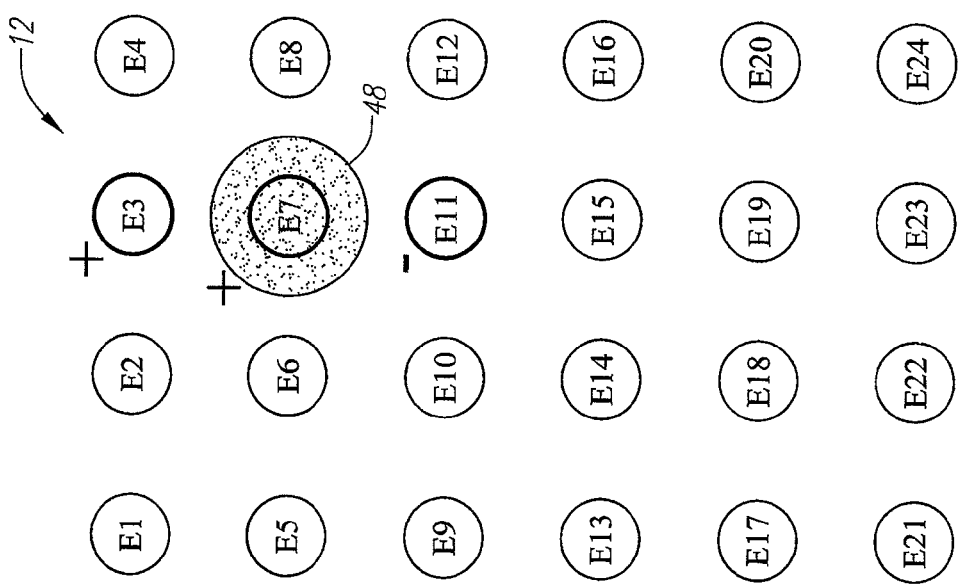

In still another embodiment, the locus of the stimulation region is electronically displaced using multiple timing channels. In particular, the electrical energy can be conveyed between different combinations of electrodes in accordance with multiple timing channels; that is, a first stimulating electrode group can be used during a first timing channel, a second stimulating electrode group can be used during a second timing channel, and so forth. The magnitude of the electrical energy conveyed in accordance with at least one of the multiple timing channels can be modified to electronically displace the locus of the stimulation region. For example, during a first timing channel, the electrode array 12 may comprise a first stimulating group of electrodes having one electrode in the third row (electrode E7) set to a "+" polarity (i.e., as an anode) and another electrode in the fourth row (electrode E11) set to a "−" polarity (i.e., as a cathode). During a second timing channel, the electrode array 12 may comprise a second stimulating group of electrodes having one electrode in the second row (electrode E3) set to a "+" polarity (i.e., as an anode) and another electrode in the fourth row (electrode E11) set to a "−" polarity (i.e., as a cathode). This polarity and grouping initially causes electrical current to flow from electrode E7 to electrode E11 in a bipolar fashion, and from electrode E3 to electrode E11 in a bipolar fashion. The first and second timing channels are simultaneously operated together, such that the electrical pulses generated at electrode E7 are interleaved between the electrical pulses generated at electrode E3, as shown in FIG. 6A, effectively resulting in a single stimulation region 48 between electrodes E3 and E7, as shown in FIG. 7A—although in any given instant of time, the locus of the stimulation region 48 will either be at a location adjacent electrode E3 or a location adjacent electrode E7.

Figure 6B:
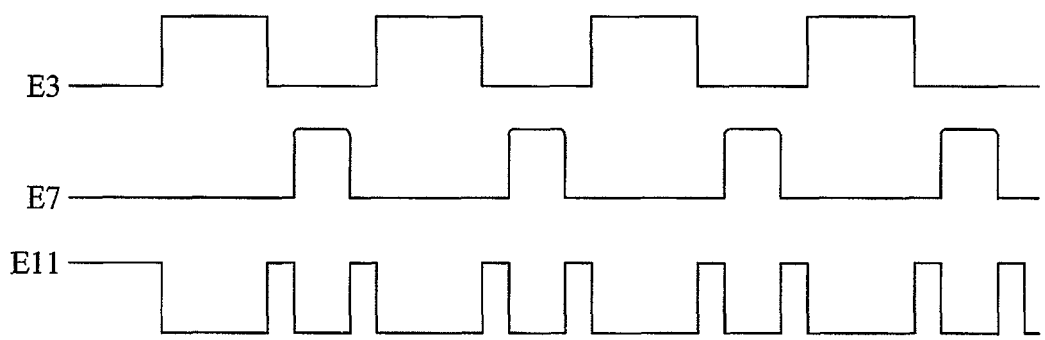
Figure 6C:
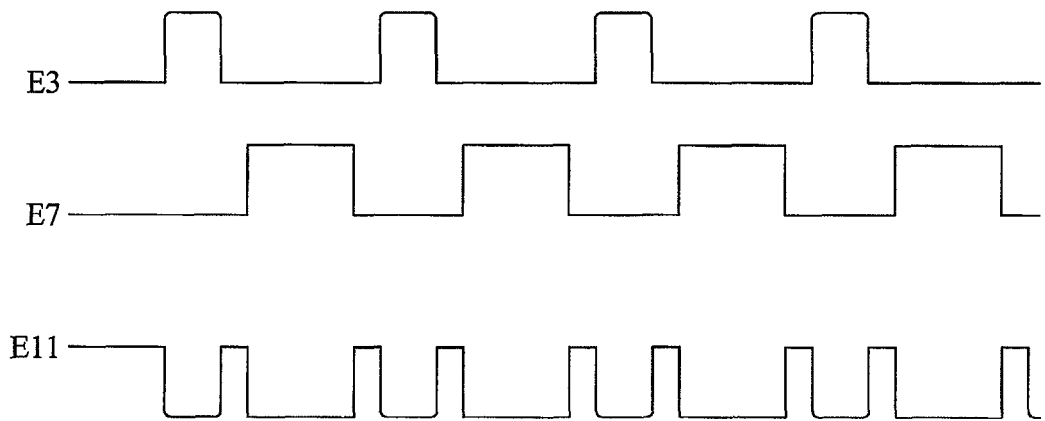
Figure 7C:
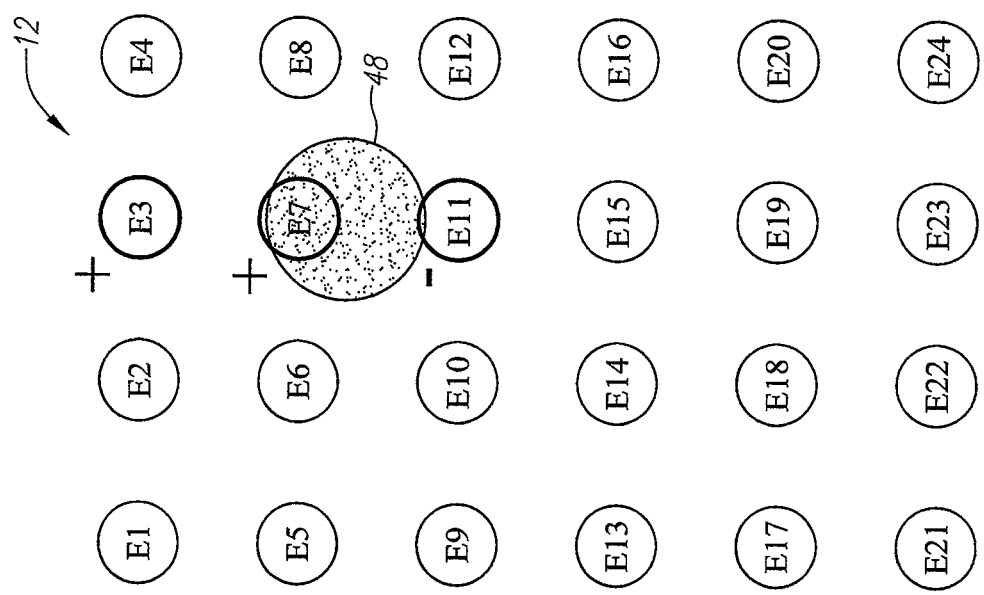

The magnitude of the electrical energy at electrode E7 during the first timing channel and/or the electrical energy at electrode E3 during the second timing channel can be modified to electronically displace the locus of the stimulation region 48. For example, if the pulse duration of the electrical energy at electrode E3 is increased, as shown in FIG. 6B, the electrical energy at electrode E3 will be increased relative to electrode E7, thereby effectively displacing the locus of the stimulation region 48 closer to electrode E3, as shown in FIG. 7B. Of course, the locus of the stimulation region 48 may be displaced closer to electrode E3 by increasing the pulse amplitude of the electrical energy at electrode E3 or by decreasing the pulse duration or pulse amplitude of the electrical energy at electrode E7. In contrast, if the pulse duration of the electrical energy at electrode E7 is increased, as shown in FIG. 6C, the electrical energy at electrode E7 will be increased relative to electrode E3, thereby effectively displacing the locus of the stimulation region closer to electrode E7, as shown in FIG. 7C. Of course, the locus of the stimulation region 48 may be displaced closer to electrode E7 by increasing the pulse amplitude of the electrical energy at electrode E7 or by decreasing the pulse duration or pulse amplitude of the electrical energy at electrode E3.

Figure 8:
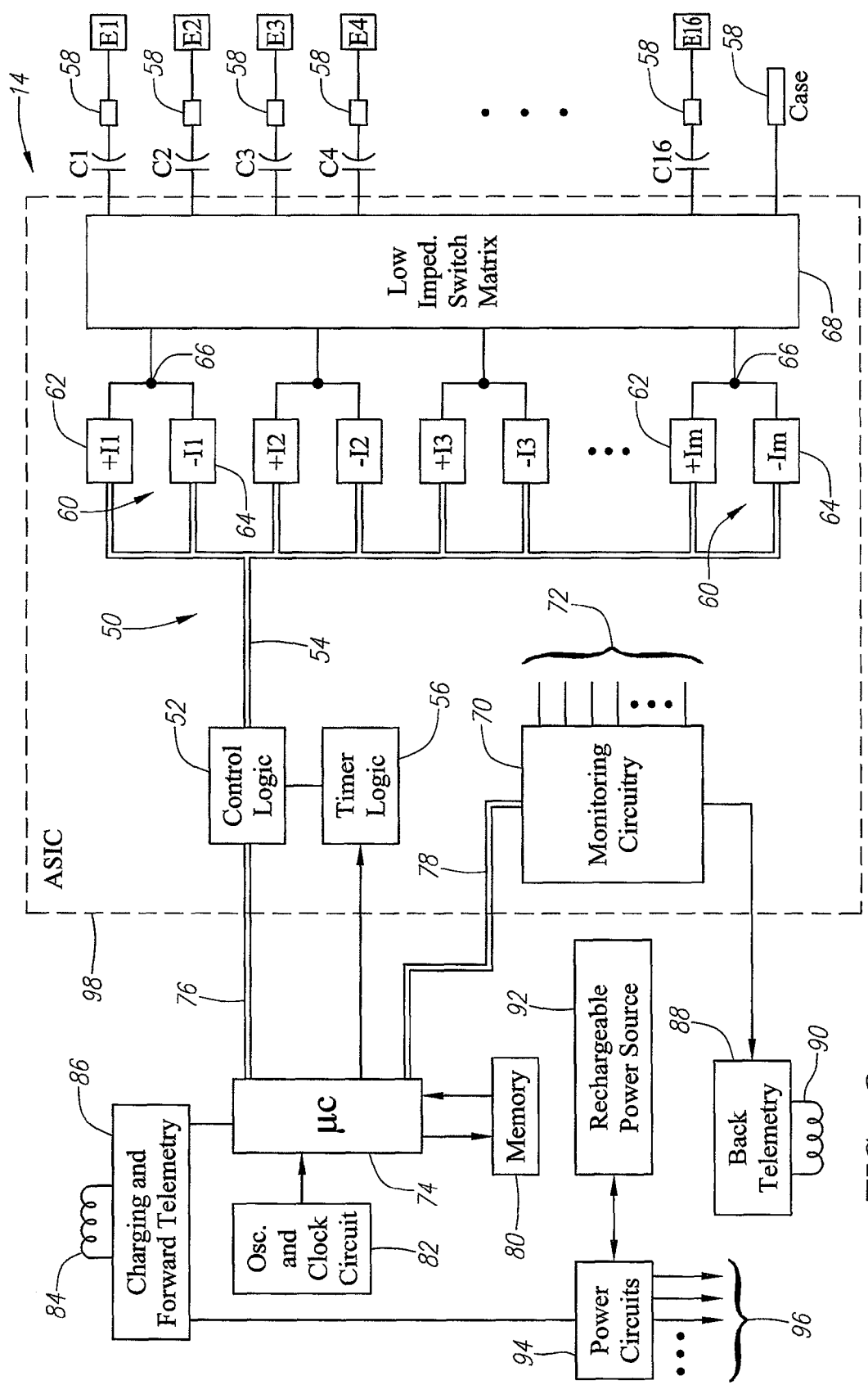
FIG. 8 is a block diagram of the internal components of the IPG of FIG. 2.

Turning next to FIG. 8, one exemplary embodiment of the IPG 14 will now be described. The IPG 14 includes stimulation output circuitry 50 configured for generating electrical stimulation energy in accordance with a defined pulsed waveform having a specified pulse amplitude, pulse rate, and pulse duration under control of control logic 52 over data bus 54. Control of the pulse rate and pulse duration of the electrical waveform is facilitated by timer logic circuitry 56, which may have a suitable resolution, e.g., 10 μs. The stimulation energy generated by the stimulation output circuitry 50 is output via capacitors C1-C24 to electrical terminals 58 corresponding to electrodes E1-E24.

In the illustrated embodiment, the stimulation output circuitry 50 comprises a plurality m independent current source pairs 60 capable of supplying stimulation energy to the electrical terminals 58 at a specified and known amperage. One current source 62 of each pair 60 functions as a positive (+) or anodic current source, while the other current source 64 of each pair 60 functions as a negative (−) or cathodic current source. The outputs of the anodic current source 62 and the cathodic current source 64 of each pair 60 are connected to a common node 66. The stimulation output circuitry 50 further comprises a low impedance switching matrix 68 through which the common node 66 of each current source pair 60 is connected to any of the electrical terminals 58 via the capacitors C1-C24.

Thus, for example, it is possible to program the first anodic current source 62 (+I1) to produce a pulse having a peak amplitude of +4 mA (at a specified rate and for a specified duration), and to synchronously program the second cathodic current source 64 (−I2) to similarly produce a pulse having a peak amplitude of −4 mA (at the same rate and pulse duration), and then connect the node 86 of the anodic current source 62 (+I1) to the electrical terminal 58 corresponding to electrode E3, and connect the node 66 of the cathodic current source 64 (−I2) to the electrical terminal 58 corresponding to electrode E1.

Hence, it is seen that each of the programmable electrical terminals 58 can be programmed to have a positive (sourcing current), a negative (sinking current), or off (no current) polarity. Further, the amplitude of the current pulse being sourced or sunk from a given electrical terminal 58 may be programmed to one of several discrete levels. In one embodiment, the current through each electrical terminal 58 can be individually set from 0 to ±10 mA in steps of 100 μA, within the output voltage/current requirements of the IPG 14. Additionally, in one embodiment, the total current output by a group of electrical terminals 58 can be up to ±20 mA (distributed among the electrodes included in the group). Moreover, it is seen that each of the electrical terminals 58 can operate in a multipolar mode, e.g., where two or more electrical terminals are grouped to source/sink current at the same time. Alternatively, each of the electrical terminals 58 can operate in a monopolar mode where, e.g., the electrical terminals 58 are configured as cathodes (negative), and case of the IPG 14 is configured as an anode (positive).

It can be appreciated that an electrical terminal 58 may be assigned an amplitude and included with any of up to k possible groups, where k is an integer corresponding to the number of timing channels, and in one embodiment, is equal to 4, and with each timing channel k having a defined pulse amplitude, pulse duration, and pulse rate. Other timing channels may be realized in a similar manner. Thus, each channel identifies which electrical terminals 58 (and thus electrodes) are selected to synchronously source or sink current, the pulse amplitude at each of these electrical terminals, and the pulse duration, and pulse rate.

In an alternative embodiment, rather than using independent controlled current sources, independently controlled voltage sources for providing stimulation pulses of a specified and known voltage at the electrical terminals 58 can be provided. The operation of this output stimulation circuitry, including alternative embodiments of suitable output circuitry for performing the same function of generating stimulation pulses of a prescribed amplitude and width, is described more fully in U.S. Pat. Nos. 6,516,227 and 6,993,384, which are expressly incorporated herein by reference.

The IPG 14 further comprises monitoring circuitry 70 for monitoring the status of various nodes or other points 72 throughout the IPG 14, e.g., power supply voltages, temperature, battery voltage, and the like. The monitoring circuitry 70 is also configured for measuring electrical data at the electrode array 12 (e.g., electrode impedance and/or electrode field potential) necessary to determine whether each of the electrodes 26 is functioning properly and is properly coupled to the IPG 14. In cases where the electrode array 12 is used to sense physiological information, the monitoring circuitry 70 may also have the appropriate circuitry (e.g., an analog/digital converter) for converting the physiological information sensed by the electrodes 26 into a form that can be subsequently analyzed. The physiological information at the electrodes 26 may be measured using any one of a variety means, but preferably is made independent of the electrical stimulation pulses, as described in U.S. Pat. Nos. 6,516,227 and 6,993,384, which are expressly incorporated herein by reference.

The IPG 14 further comprises processing circuitry in the form of a microcontroller (μC) 74 that controls the control logic 52 over data bus 76, and obtains status data, and optionally physiological information, from the monitoring circuitry 70 via data bus 78. The IPG 14 additionally controls the timer logic 56. The IPG 14 further comprises memory 80 and an oscillator and clock circuit 82 coupled to the microcontroller 74. Thus, the microcontroller 74, in combination with the memory 80 and oscillator and clock circuit 82, comprise a microprocessor system that carries out functions in accordance with a suitable program stored in the memory 80. Alternatively, for some applications, the functions provided by the microprocessor system may be carried out by a suitable state machine.

The microcontroller 74 generates the necessary control and status signals, which allow the microcontroller 74 to control the operation of the IPG 14 in accordance with the operating program and stimulation parameters stored in the memory 80. In controlling the operation of the IPG 14, the microcontroller 74 is able to individually generate stimulus pulses at the electrodes 26 using the stimulation output circuitry 50, in combination with the control logic 52 and timer logic 56, thereby allowing each electrode 12 to be paired or grouped with other electrodes 26, including the monopolar case electrode, and to control and modify the polarity, pulse amplitude, pulse rate, pulse duration, and channel through which the current stimulus pulses are provided. In the case wherein the IPG 14 processes physiological information (either sensed at the electrodes 26 via the monitoring circuitry 70 or sensed using a separate monitor), the algorithm used to electronically displace the locus of the stimulation region based on the sensed physiological information may be stored in the memory 80 for execution by the microcontroller 74 to appropriately control the stimulation output circuitry 50 via adjustment of the stimulation parameters. In this case, the microcontroller 74 will determine the stimulation parameters, including the electrode combination and individual amplitudes of the electrical energy at the electrodes 16, necessary to electronically displace the locus of the stimulation region in an optimum or otherwise more effective manner, and control the stimulation output circuitry 50 in accordance with these stimulation parameters.

The IPG 14 further comprises an alternating current (AC) receiving coil 84 for receiving programming data (e.g., the operating program and/or stimulation parameters) from the RC 16 in an appropriate modulated carrier signal, and charging and forward telemetry circuitry 86 for demodulating the carrier signal it receives through the AC receiving coil 84 to recover the programming data, which programming data is then stored within the memory 80, or within other memory elements (not shown) distributed throughout the IPG 14.

The IPG 14 further comprises back telemetry circuitry 88 and an alternating current (AC) transmission coil 90 for sending informational data sensed through the monitoring circuitry 70 to the RC 16. The back telemetry features of the IPG 14 also allow its status to be checked. For example, any changes made to the stimulation parameters are confirmed through back telemetry, thereby assuring that such changes have been correctly received and implemented within the IPG 14. Moreover, upon interrogation by the RC 16, all programmable settings stored within the IPG 14 may be uploaded to the RC 16.

The IPG 14 further comprises a rechargeable power source 92 and power circuits 94 for providing the operating power to the IPG 14. The rechargeable power source 92 may, e.g., comprise a lithium-ion or lithium-ion polymer battery. The rechargeable battery 92 provides an unregulated voltage to the power circuits 94. The power circuits 94, in turn, generate the various voltages 96, some of which are regulated and some of which are not, as needed by the various circuits located within the IPG 14. The rechargeable power source 92 is recharged using rectified AC power (or DC power converted from AC power through other means, e.g., efficient AC-to-DC converter circuits, also known as "inverter circuits") received by the AC receiving coil 84. To recharge the power source 92, an external charger (not shown), which generates the AC magnetic field, is placed against, or otherwise adjacent, to the patient's skin over the implanted IPG 14. The AC magnetic field emitted by the external charger induces AC currents in the AC receiving coil 84. The charging and forward telemetry circuitry 86 rectifies the AC current to produce DC current, which is used to charge the power source 92. While the AC receiving coil 84 is described as being used for both wirelessly receiving communications (e.g., programming and control data) and charging energy from the external device, it should be appreciated that the AC receiving coil 84 can be arranged as a dedicated charging coil, while another coil, such as coil 90, can be used for bi-directional telemetry.

As shown in FIG. 8, much of the circuitry included within the IPG 14 may be realized on a single application specific integrated circuit (ASIC) 98. This allows the overall size of the IPG 14 to be quite small, and readily housed within a suitable hermetically-sealed case. Alternatively, most of the circuitry included within the IPG 14 may be located on multiple digital and analog dies, as described in U.S. patent application Ser. No. 11/177,503, filed Jul. 8, 2005, which is incorporated herein by reference in its entirety. For example, a processor chip, such as an application specific integrated circuit (ASIC), can be provided to perform the processing functions with on-board software. An analog IC (AIC) can be provided to perform several tasks necessary for the functionality of the IPG 14, including providing power regulation, stimulus output, impedance measurement and monitoring. A digital IC (DigIC) may be provided to function as the primary interface between the processor IC and analog IC by controlling and changing the stimulus levels and sequences of the current output by the stimulation circuitry in the analog IC when prompted by the processor IC.

It should be noted that the diagram of FIG. 8 is functional only, and is not intended to be limiting. Those of skill in the art, given the descriptions presented herein, should be able to readily fashion numerous types of IPG circuits, or equivalent circuits, that carry out the functions indicated and described. Additional details concerning the above-described and other IPGs may be found in U.S. Pat. No. 6,516,227, U.S. Patent Publication No. 2003/0139781, and U.S. patent application Ser. No. 11/138,632, entitled "Low Power Loss Current Digital-to-Analog Converter Used in an Implantable Pulse Generator," which are expressly incorporated herein by reference. It should be noted that rather than an IPG, the SCS system 10 may alternatively utilize an implantable receiver-stimulator (not shown) connected to the stimulation leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

As briefly discussed above, stimulation parameters can be programmed into or otherwise modified within the IPG 14 by the RC 16 and/or CP 18, thereby setting or otherwise changing the characteristics of the electrical stimulation energy generated and output by the IPG 14 to the electrodes 26. In the illustrated embodiment, this is accomplished by telemetrically transmitting instructions containing the stimulation parameters from the IPG 14 and/or CP 18 to the IPG 14. Alternatively, instructions without the stimulation parameters can be transmitted from the RC 16 and/or CP 18 to the IPG 14 to otherwise change the stimulation parameters stored in the IPG 14.

Figure 9:
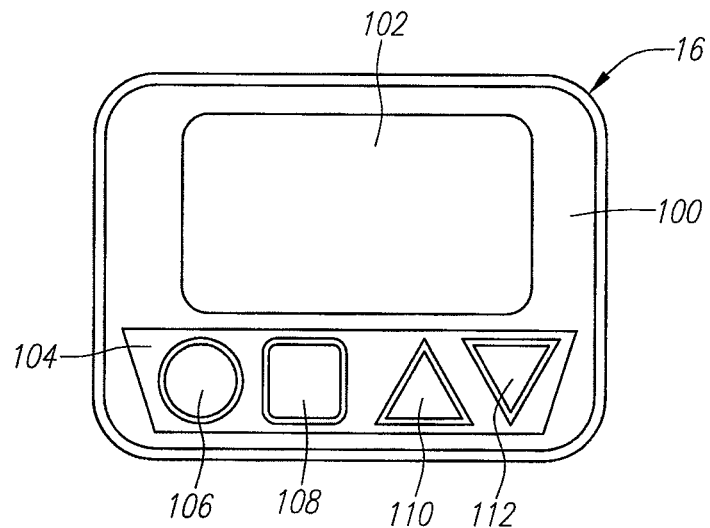
FIG. 9 is a plan view of a hand-held remote control (RC) that can be used in the brain stimulation system of FIG. 1.

Referring now to FIG. 9, one exemplary embodiment of an RC 16 will now be described. As previously discussed, the RC 16 is capable of communicating with the IPG 14, CP 18, or ETS 20. The RC 16 comprises a casing 100, which houses internal componentry (including a printed circuit board (PCB)), and a lighted display screen 102 and button pad 104 carried by the exterior of the casing 100. In the illustrated embodiment, the display screen 102 is a lighted flat panel display screen, and the button pad 104 comprises a membrane switch with metal domes positioned over a flex circuit, and a keypad connector connected directly to a PCB. In an optional embodiment, the display screen 102 has touchscreen capabilities. The button pad 104 includes a multitude of buttons 106, 108, 110, and 112, which allow the IPG 14 to be turned ON and OFF, provide for the adjustment or setting of stimulation parameters within the IPG 14, and provide for selection between screens.

In the illustrated embodiment, the button 106 serves as an ON/OFF button that can be actuated to turn the IPG 14 ON and OFF. The button 108 serves as a select button that allows the RC 16 to switch between screen displays and/or parameters. The buttons 110 and 112 serve as up/down buttons that can actuated to increment or decrement any of stimulation parameters of the pulse generated by the IPG 14, including pulse amplitude, pulse duration, and pulse rate. For example, the selection button 108 can be actuated to place the RC 16 in an "Pulse Amplitude Adjustment Mode," during which the pulse amplitude can be adjusted via the up/down buttons 110, 112, a "Pulse duration Adjustment Mode," during which the pulse duration can be adjusted via the up/down buttons 110, 112, and a "Pulse Rate Adjustment Mode," during which the pulse rate can be adjusted via the up/down buttons 110, 112. Alternatively, dedicated up/down buttons can be provided for each stimulation parameter. Rather than using up/down buttons, any other type of actuator, such as a dial, slider bar, or keypad, can be used to increment or decrement the stimulation parameters.

While the present inventions contemplate that the IPG 14 may, itself, process or analyze the sensed physiological information in order to effect electronic displacement of the locus of the stimulation region, the RC 16 may optionally have this capability. To this end, the selection button 108 can be actuated to place the RC 16 within an "Automated Stimulation Region Placement" mode, during which the RC 16 determines the stimulation parameters, including the electrode combination and individual amplitudes of the electrical energy at the electrodes 16, necessary to electronically displace the locus of the stimulation region in an optimum or otherwise more effective manner.

Figure 10:
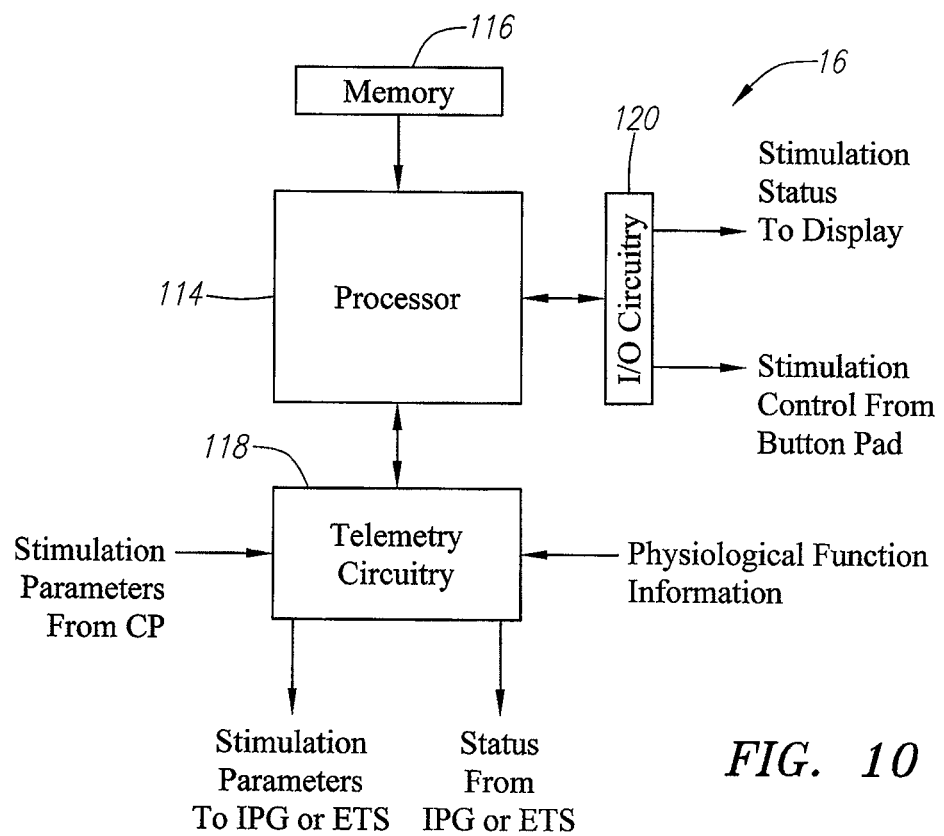
FIG. 10 is a block diagram of the internal components of the RC of FIG. 9.

Referring to FIG. 10, the internal components of an exemplary RC 16 will now be described. The RC 16 generally includes a processor 114 (e.g., a microcontroller), memory 116 that stores an operating program for execution by the processor 114, as well as stimulation parameters, input/output circuitry, and in particular, telemetry circuitry 118 for outputting stimulation parameters to the IPG 14 and receiving status information from the IPG 14. The telemetry circuitry 118 can also be used to receive stimulation parameters from the CP 18 and/or physiological information from the IPG 14 or other monitoring device. The RC 16 further comprises input/output circuitry 120 for receiving stimulation control signals from the button pad 104 and transmitting status information to the display screen 102 (shown in FIG. 9). As well as controlling other functions of the RC 16, which will not be described herein for purposes of brevity, the processor 114 generates a plurality of stimulation parameter sets that define the pulse amplitude, pulse duration, and pulse rate in response to the user operation of the button pad 104. In the case where the RC 16 is capable of determining the stimulation parameters based on the sensed physiological information, the stimulation parameter sets generated by the processor 114, which may contain the electrode combinations, as well as the individual amplitudes of the electrodes, may also correspond to the different loci of the stimulation region. These new stimulation parameter sets would then be transmitted to the IPG 14 via the telemetry circuitry 118, thereby adjusting the stimulation parameters stored in the IPG 14 and/or programming the IPG 14. The telemetry circuitry 118 can also be used to receive stimulation parameters from the CP 18. Further details of the functionality and internal componentry of the RC 16 are disclosed in U.S. Pat. No. 6,895,280, which has previously been incorporated herein by reference.

As briefly discussed above, modifying and programming the stimulation parameters in the programmable memory of the IPG 14 after implantation can also be performed by a physician or clinician using the CP 18, which can directly communicate with the IPG 14 or indirectly communicate with the IPG 14 via the RC 16. That is, the CP 18 can be used by the physician or clinician to modify operating parameters of the electrode array 12 near the spinal cord. As shown in FIG. 1, the overall appearance of the CP 18 is that of a laptop personal computer (PC), and in fact, may be implemented using a PC that has been appropriately configured to include a directional-programming device and programmed to perform the functions described herein. Thus, the programming methodologies can be performed by executing software instructions contained within the CP 18. Alternatively, such programming methodologies can be performed using firmware or hardware. In any event, the CP 18 may actively control the characteristics of the electrical stimulation generated by the IPG 14 (or ETS 20) to allow the optimum stimulation parameters to be determined based on patient feedback and to subsequently program the IPG 14 (or ETS 20) with the optimum stimulation parameters. Thus, the functionality of the CP 18 is similar to that of the RC 18, with the exception that it greatly simplifies the programming of the optimum stimulation parameters. Further details discussing CPs and other programming devices are disclosed in U.S. Pat. Nos. 6,393,325 and 6,909,917, which are expressly incorporated herein by reference.

Figure 11:
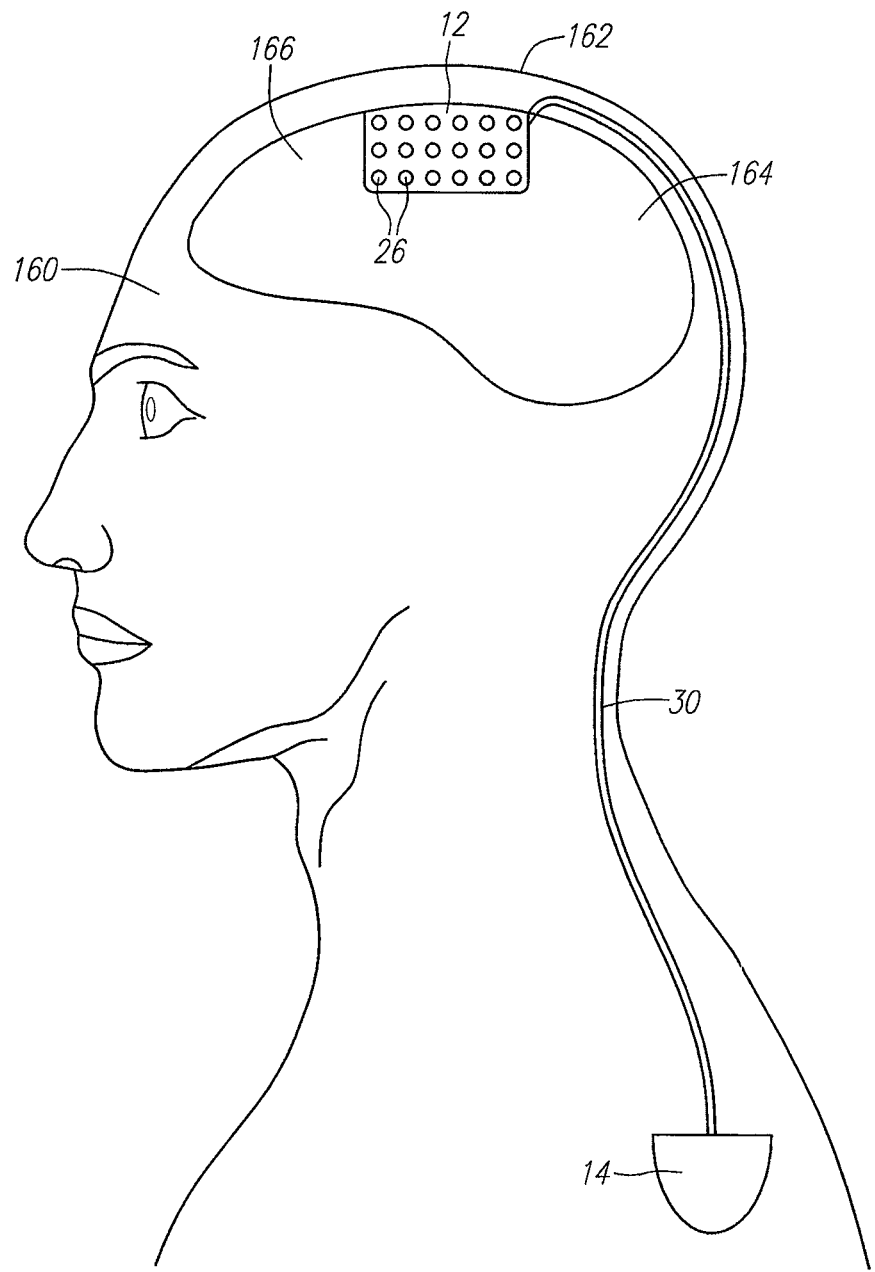
FIG. 11 is a plan view of the brain stimulation system of FIG. 1 in use with a patient.

Having described the structure and function of the SCS system 10, a method of implanting and operating the system 10 will now be described. Referring to FIG. 11, the electrode array 12 is conventionally implanted within the head 162 of a patient 160. The preferred placement of the electrode array 12 is adjacent to the cortex 166 of the brain 164, and preferably underneath the dura mater (not shown). Alternatively, electrode lead(s) may be implanted within the deep regions of the brain. The ETS 20 may then be coupled to the electrode array 12 via the percutaneous lead extension 36 and external cable 38 (not shown in FIG. 11), and then operated to deliver electrical stimulation energy to the electrodes 26 to create a stimulation region within the brain 164. Physiological information is then sensed, either by the electrode array 12 or a separate device, and the locus of the stimulation region is electronically displaced based on the sensed physiological in any of the manner described above. The pulse parameters of the waveform (including the pulse amplitude, pulse duration, and pulse rate) may be further modified under control of the CP 18, thereby changing the characteristics of the electrical stimulation energy delivered from the electrodes 26 to the tissue, and allowing the efficacy of the stimulation provided to the patient 160 to be tested. The CP 18 can then be used to program the optimum stimulation parameters into the ETS 20, including those stimulation parameters that optimally place the locus of the stimulation region.

After the trial period is over (typically 1-2 weeks), the IPG 14 is implanted within the patient 160 (typically either in the chest region, abdomen, or above the buttocks) and coupled to the electrode array 12 via the lead extension 30. In the same manner briefly described above with respect to the ETS 20, the IPG 14 can then be operated and programmed with the optimum stimulation parameters under control of the CP 18. Under control of the patient, the RC 16 can subsequently be used to select stimulation programs or otherwise modify the stimulation parameters previously programmed into the IPG 14 to change the therapy, including electronically displacing the locus of the stimulation region.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A neurostimulation system, comprising:
   a plurality of electrical terminals configured for being electrically coupled to a plurality of electrodes;
   output stimulation circuitry configured for conveying electrical energy between the electrodes, thereby creating a stimulation region in tissue of a patient when the electrodes are located adjacent the tissue;
   monitoring circuitry configured for sensing a cognitive brain signal; and
   control circuitry configured for analyzing the sensed cognitive brain signal and for controlling the output stimulation circuitry to displace a locus of the stimulation region relative to the tissue based on the analysis of the sensed cognitive brain signal.

2. The system of claim 1, wherein the output stimulation circuitry is configured for conveying the electrical energy between the electrical terminals to change the status of a dysfunction suffered by the patient, and the sensed cognitive brain signal is indicative of the changed status of the dysfunction.

3. The system of claim 1, wherein the sensed cognitive brain signal is indicative of a desire of the patient to displace the locus of the stimulation region.

4. The system of claim 1, wherein the control circuitry is configured for automatically controlling the output stimulation circuitry to displace the locus of the stimulation region in response to a change in the sensed cognitive brain signal.

5. The system of claim 1, wherein the output stimulation circuitry is configured for conveying the electrical energy between the electrodes in accordance with a single timing channel to create the stimulation region, and the control circuitry is configured for controlling the output stimulation circuitry to displace the locus of the stimulation region by modifying an electrode combination for the single timing channel.

6. The system of claim 1, wherein the output stimulation circuitry is configured for conveying the electrical energy between the electrodes in accordance with a single timing channel to create the stimulation region, and the control circuitry is configured for controlling the output stimulation circuitry to displace the locus of the stimulation region by shifting electrical current between at least two of the electrodes for the single timing channel.

7. The system of claim 1, wherein the output stimulation circuitry is configured for conveying the electrical energy between the electrodes in accordance with a plurality of timing channels to create the stimulation region, and the control circuitry is configured for controlling the output stimulation circuitry to displace the locus of the stimulation region by modifying the relative magnitude of the electrical energy conveyed in accordance with the timing channels.

8. The system of claim 1, further comprising a case, wherein the electrical terminals and output stimulation circuitry are contained in the case to form a neurostimulator.

9. The system of claim 8, wherein the monitoring circuitry is contained within the case.

10. The system of claim 8, wherein the control circuitry is contained within the case.

11. The system of claim 8, wherein the neurostimulator is implantable.

12. The system of claim 8, wherein the control circuitry is configured for identifying changes in amplitude in components of a spectrum of the sensed cognitive brain signal.

13. The system of claim 12, wherein the spectrum of the sensed cognitive brain signals comprises one or more of $\mu$, $\beta$, and $\gamma$ rhythms.

14. The system of claim 13, wherein the one or more of $\mu$, $\beta$, and $\gamma$ rhythms comprises a $\gamma$ rhythm.

15. A method of providing therapy to a patient using the neurostimulation system of claim 1, comprising:
   conveying via the output circuitry electrical energy between electrodes to create the stimulation region in the tissue adjacent the electrodes;
   sensing via the monitoring circuitry the cognitive brain signal;
   analyzing via the control circuitry the sensed cognitive brain signal and to automatically displacing a locus of the stimulation region relative to the tissue based on the analysis of the sensed cognitive brain signal.

16. The method of claim 15, wherein the tissue is brain tissue.

17. The method of claim 16, wherein the brain tissue is cortical brain tissue.

18. The method of claim 15, wherein the patient suffers from a dysfunction, and the electrical energy is conveyed between the electrodes to change the status of the dysfunction.

19. The method of claim 18, wherein the dysfunction is a neurological disorder.

20. The method of claim 18, wherein the sensed cognitive brain signal is indicative of the changed status of the dysfunction.

21. The method of claim 15, wherein the sensed cognitive brain signal is indicative of a desire of the patient to displace the locus of the stimulation region.

22. The method of claim 15, wherein the locus of the stimulation region is automatically displaced in response to a change in the sensed cognitive brain signal.

23. The method of claim 15, wherein the electrical energy is conveyed between the electrodes in accordance with a single timing channel to create the stimulation region, and the locus of the stimulation region is automatically displaced by modifying an electrode combination for the single timing channel.

24. The method of claim 15, wherein the electrical energy is conveyed between the electrodes in accordance with a single timing channel to create the stimulation region, and the locus of the stimulation region is automatically displaced by shifting electrical current between at least two of the electrodes for the single timing channel.

25. The method of claim 15, wherein the electrical energy is conveyed between the electrodes in accordance with a plurality of timing channels to create the stimulation region, and the locus of the stimulation region is automatically displaced by modifying the relative magnitude of the electrical energy conveyed in accordance with the timing channels.

26. The method of claim 15, wherein the cognitive brain signal is an EEG or ECoG signal obtained from a brain region that can be correlated to intentions of the patient.

27. The method of claim 26, wherein the brain region controls imagery of certain actions.

28. The method of claim 15, further comprising identifying changes in amplitude in components of a spectrum of the sensed cognitive brain signal.

29. The method of claim 28, wherein the spectrum of the sensed cognitive brain signals comprises one or more of $\mu$, $\beta$, and $\gamma$ rhythms.

30. The method of claim 29, wherein the one or more of $\mu$, $\beta$, and $\gamma$ rhythms comprises a $\gamma$ rhythm.

* * * * *